(12) United States Patent
Lira et al.

(10) Patent No.: US 10,028,510 B2
(45) Date of Patent: Jul. 24, 2018

(54) DIG-17 INSECTICIDAL CRY TOXINS

(71) Applicant: Dow AgroSciences LLC, Indianapolis, IN (US)

(72) Inventors: Justin M. Lira, Zionsville, IN (US); Holly Jean Butler, Indianapolis, IN (US); Timothy D. Hey, Zionsville, IN (US); Doug A. Smith, Noblesville, IN (US); Kenneth Narva, Zionsville, IN (US); Aaron T. Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 162 days.

(21) Appl. No.: 14/831,301

(22) Filed: Aug. 20, 2015

(65) Prior Publication Data

US 2016/0058017 A1 Mar. 3, 2016

Related U.S. Application Data

(60) Provisional application No. 62/043,059, filed on Aug. 28, 2014.

(51) Int. Cl.
| | |
|---|---|
| *C12N 15/82* | (2006.01) |
| *C12N 15/32* | (2006.01) |
| *C07K 14/325* | (2006.01) |
| *A01N 63/02* | (2006.01) |
| *A01N 37/46* | (2006.01) |

(52) U.S. Cl.
CPC ............. *A01N 63/02* (2013.01); *A01N 37/46* (2013.01); *C07K 14/325* (2013.01); *C12N 15/8286* (2013.01); *C07K 2319/55* (2013.01)

(58) Field of Classification Search
CPC .......................... C12N 15/8286; C07K 14/325
See application file for complete search history.

(56) References Cited

U.S. PATENT DOCUMENTS

| | | | |
|---|---|---|---|
| 5,527,883 A | 6/1996 | Thompson et al. | |
| 5,593,881 A | 1/1997 | Thompson et al. | |
| 5,840,554 A | 11/1998 | Thompson et al. | |
| 5,932,209 A | 8/1999 | Thompson et al. | |
| 6,673,990 B2 | 1/2004 | Cardineau et al. | |
| 7,605,304 B2 * | 10/2009 | Abad .................. | C07K 14/325 536/23.71 |
| 8,188,036 B2 | 5/2012 | Abad et al. | |
| 8,299,217 B2 | 10/2012 | Heinrichs | |
| 8,304,605 B2 | 11/2012 | Lira et al. | |
| 9,006,520 B2 | 4/2015 | Lira et al. | |
| 9,139,844 B2 | 9/2015 | Meade et al. | |
| 9,487,798 B2 | 11/2016 | Lira et al. | |
| 2004/0210963 A1 | 10/2004 | Abad et al. | |

OTHER PUBLICATIONS

Tounsi et al (J. Appl. MicrobioL 95:23-28; 2003).*
De Maagd et al (Appl Environ. Microbiol 65:4369-4374, 1999).*
Aronson et al ((FEMS Microbiol. Lett. 2001, 195:1-8).*
Bravo et al (Microbial Biotechnology, 6, (2012) 17-26.*
International Search Report for PCT/US2015/046088, dated Jan. 19, 2016.
Crickmore et al. (1998) "Revision of the Nomenclature for the Bacillus thuringiensis Pesticidal crystal Proteins," Micribiology and Molecular Biology Reviews, 62(3):807-813.
Bravo et al. (2007) "Mode of Action of Bacillus thuringensis Cry and Cyt toxins and their potential for insect control" Toxicon, 49(4): 423-435.

* cited by examiner

*Primary Examiner* — Lee A Visone
(74) *Attorney, Agent, or Firm* — Marcos P. Rivas

(57) ABSTRACT

DIG-17 insecticidal toxins, polynucleotides encoding such toxins, use of such toxins to control pests, and transgenic plants that produce such toxins are disclosed.

17 Claims, No Drawings

SEQUENCE LISTING

<160> NUMBER OF SEQ ID NOS: 8

<210> SEQ ID NO 1
<211> LENGTH: 3474
<212> TYPE: DNA
<213> ORGANISM: Bacillus thuringiensis

<400> SEQUENCE: 1

```
atgagtccaa ataatcaaaa tgaatatgaa attatagatg cgacaccttc tacttctgta      60
tccaataatt ctaacagata ccctttttgcg aatgagtcaa caaatgcgtt acaaaatatg     120
aattataaag attatttaag aatgtctggg ggaaatgcta gtgaatatcc tggttcacct     180
gaggcattta taagcgagca ggatgcagct aaggccgcaa ttgatctaat aggtacatta     240
ctaacagggt taggactgcc gtttgttggg ccgatagtgg gtctttatac tcaacttatt     300
gatattctgt ggcctttcagg ggaaaagagt caatgggaaa tttttatgga acaagtagaa     360
gtactcgtta atcagagaat agaagaggcc gtaaagagta aggcgattgc ggaattagaa     420
gggttaggaa acaacttcca attatatcta acggcacttg aagaatggca agaaaaccca     480
aatggtgcaa gagcttacg agatgttcga aatcgatttg aaatcctgga tagtttattt     540
acgcaatata tgccatcttt tcgagtggca aaatttgaag taccgcttct tatagtatat     600
acaatggcag caaaccttca tttactttta ttaaaggacg catcaatttt tggagaagaa     660
tggggattgt caacaactac tattaataac tattatgatc gtcaaatgaa acttaccgca     720
gaatattctg attattgtgt aaagtggtat aaaactggtt tacaaaaatt aattggcgtg     780
agcgctaaac aatgggtagc atataatcgt ttccgtagag aaatgacatt ggcggtgtta     840
gatcttgtgt cgttatttcc aaactatgac gcgcgtacgt atccaattca aacgaaagcc     900
caacttacaa gggaattgta tacagatcca ctgggtcgcg taaatgtgcc ttcaattggt     960
tcctggtatg acaaagcacc ttctttcgga gtgatagaag catccgttat tcgaccaccc    1020
catgtatttg attttataac aggactcaca gtgtatacac aatcacgtag cgtttctacc    1080
gctcattata aagacattg ggctggtcat aaaatacgct atcgtcggac tctggatgtt    1140
aataataatg aacagatgta tggaactaat gaaaatctac acagcactag tgtgtatgat    1200
tttacggatt atgatattta caagacgtta tcaaaagatg cggtgctctt tgatattgtt    1260
```

```
ttccctgttg gtacgtatat attttttgga atgccagaag tcgagttttt catggtaaac    1320
caattgaata ataccagaaa gacgttaacg tataaaccag gttccaaaga tattatagag    1380
cggacaagag attcggaatt agaattgcct ccagaaactt cagatcaacc aaattatgag    1440
tcatatagcc atagattatg tcatatcaca agtattcccg cgacgggttc aactaccgga    1500
ttagtacctg tgttttcttg gacacatcga agtgcagatt taaacaatac aatatattca    1560
gataaaatca ctcaaattcc ggctgttaaa agttgggact attctagtcc tggttcttat    1620
ataaagggac caggacatac aggaggagat ttactacagt atataagaag gggttctgca    1680 ggagggctt tcctaaatcg atataggtat acattagaaa aagcagggga atatcttgta     1740
aggttgaggt atgctgctga tgcagatatt gtattgtatg taggcggtgt taagattcag    1800
atgccaaaaa caatgaaccc aggtgaggat ctaacattta aaactttaa agttgcagca     1860 gctaatagta ccttgaattt attagagaat ggaagtcttg cgttgcaata tttatattta    1920
aatgatccta attctacatt ggctggtacc gtttatgttg atcgaatcga attcgcccca    1980
gcagatgaga catatgaagc ggaacaagat ttagaagcgg cgaagaaagc agtgaatgcc    2040 ttgttttacga atacaaaaga tggattacga ccaggggtaa cggattatga agtgaatcag    2100
gcggcaaact tagtggaatg cctatcggat gatttgtatc caaatgaaaa acgattgtta    2160
tttgatgcag tgagagaggc aaaacgtctc agtgaggcac gtaatttact acaagatcca    2220
gatttccaag agataaatgg cgaaatgga tggacgggaa gtacgggaat tgagattgga     2280
gaaggggatg ctgtatttaa agggcgttat ctaagcctac caggtgcgag agaaaattgat   2340 acggaaacgt atccaacata tttatatcaa aaaatagagg taagtcgatt aaaaccatac    2400
acaagatata gactaaaagg atttgtggga agtagtcaag gattagaaat ttatacgata    2460
catcaccaaa cgaatcgaat tgtaaaaaat gtaccaaatg atttacagcc agatgtatct    2520
cctgttaacg ctgatggtag tatcaatcga tgcagcgaac aaaagtatgt gaatagccgt    2580
ttaaaaatag aaaaccgttc tggtgacgcg catgagttct ctatccctat tgatacgggt    2640
gaaattgatt acaatgaaaa tgcaggaatt tgggttggat ttaagattac ggacccagag    2700
ggatacgcaa cacttggaaa tcttgaattg gtcgaagagg gacctttgtc aggagacgca    2760
ttagaacgct tgcaacgaga agaacaacag tggaagattc aaatgacaag aagacgtgaa    2820
gagacagata gaagatacat ggcatcgaaa caagcggtag atcgtttata tgtcgattat    2880
caggatcagc aattgaatcc ggttgtagag attacagatc ttactgcggc tcaaaacctg    2940
atacagtcca ttccttacgt gtataacgaa atgttcccag aaataccagg gatgaactat    3000
acgaagttta cagaattaac agatcgactc caacaagcct atagtttgta tgatcaacga    3060
aatgccatac caaatggtga ttttcgaaat ggtttaagta attggaatgc aacgcctggt    3120
gtggatatac aacaaatcaa taatacatct gtccttgtaa ttccaaactg ggatgagcaa    3180
gtttctcaac agtttacagt tcaaccgaat caaagatatg tgttacgagt taccgcaaga    3240
aaagaaggga taggaaatgg atatgtaagt atccgtgatg gtggaaatca aacagaaaca    3300
cttactttta atgcaaacga atatgataca aatggtgtgt ataatgacca aactggctat    3360
atcacaaaaa cagtgacatt catcccgtat acagatcaaa tgtggattga aataagtgaa    3420
acagaaggta tgttctatat agaaagtgta gaattgattg tagacgtaga gtaa          3474
```

<210> SEQ ID NO 2
<211> LENGTH: 1157
<212> TYPE: PRT
<213> ORGANISM: Bacillus thuringiensis

<400> SEQUENCE: 2

```
Met Ser Pro Asn Asn Gln Asn Glu Tyr Glu Ile Ile Asp Ala Thr Pro
1               5                   10                  15

Ser Thr Ser Val Ser Asn Asn Ser Asn Arg Tyr Pro Phe Ala Asn Glu
            20                  25                  30

Ser Thr Asn Ala Leu Gln Asn Met Asn Tyr Lys Asp Tyr Leu Arg Met
        35                  40                  45

Ser Gly Gly Asn Ala Ser Glu Tyr Pro Gly Ser Pro Glu Ala Phe Ile
    50                  55                  60

Ser Glu Gln Asp Ala Ala Lys Ala Ala Ile Asp Leu Ile Gly Thr Leu
65                  70                  75                  80

Leu Thr Gly Leu Gly Leu Pro Phe Val Gly Pro Ile Val Gly Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Val Leu Val Asn Gln Arg Ile Glu
        115                 120                 125

Glu Ala Val Lys Ser Lys Ala Ile Ala Glu Leu Glu Gly Leu Gly Asn
    130                 135                 140

Asn Phe Gln Leu Tyr Leu Thr Ala Leu Glu Glu Trp Gln Glu Asn Pro
145                 150                 155                 160

Asn Gly Ala Arg Ala Leu Arg Asp Val Arg Asn Arg Phe Glu Ile Leu
                165                 170                 175

Asp Ser Leu Phe Thr Gln Tyr Met Pro Ser Phe Arg Val Ala Lys Phe
            180                 185                 190

Glu Val Pro Leu Leu Ile Val Tyr Thr Met Ala Ala Asn Leu His Leu
        195                 200                 205

Leu Leu Leu Lys Asp Ala Ser Ile Phe Gly Glu Glu Trp Gly Leu Ser
    210                 215                 220

Thr Thr Thr Ile Asn Asn Tyr Tyr Asp Arg Gln Met Lys Leu Thr Ala
225                 230                 235                 240

Glu Tyr Ser Asp Tyr Cys Val Lys Trp Tyr Lys Thr Gly Leu Gln Lys
                245                 250                 255

Leu Ile Gly Val Ser Ala Lys Gln Trp Val Ala Tyr Asn Arg Phe Arg
            260                 265                 270

Arg Glu Met Thr Leu Ala Val Leu Asp Leu Val Ser Leu Phe Pro Asn
        275                 280                 285

Tyr Asp Ala Arg Thr Tyr Pro Ile Gln Thr Lys Ala Gln Leu Thr Arg
    290                 295                 300

Glu Leu Tyr Thr Asp Pro Leu Gly Ala Val Asn Val Pro Ser Ile Gly
305                 310                 315                 320

Ser Trp Tyr Asp Lys Ala Pro Ser Phe Gly Val Ile Glu Ala Ser Val
                325                 330                 335

Ile Arg Pro Pro His Val Phe Asp Phe Ile Thr Gly Leu Thr Val Tyr
            340                 345                 350

Thr Gln Ser Arg Ser Val Ser Thr Ala His Tyr Ile Arg His Trp Ala
        355                 360                 365

Gly His Lys Ile Arg Tyr Arg Arg Thr Leu Asp Val Asn Asn Asn Glu
    370                 375                 380

Gln Met Tyr Gly Thr Asn Glu Asn Leu His Ser Thr Ser Val Tyr Asp
385                 390                 395                 400

Phe Thr Asp Tyr Asp Ile Tyr Lys Thr Leu Ser Lys Asp Ala Val Leu
```

```
            405                 410                 415
Phe Asp Ile Val Phe Pro Val Gly Thr Tyr Ile Phe Phe Gly Met Pro
                420                 425                 430

Glu Val Glu Phe Phe Met Val Asn Gln Leu Asn Asn Thr Arg Lys Thr
            435                 440                 445

Leu Thr Tyr Lys Pro Gly Ser Lys Asp Ile Ile Glu Arg Thr Arg Asp
        450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Ser Trp Asp Tyr Ser Ser Pro Gly Ser Tyr Ile Lys Gly Pro
530                 535                 540

Gly His Thr Gly Gly Asp Leu Leu Gln Tyr Ile Arg Arg Gly Ser Ala
545                 550                 555                 560

Gly Gly Ala Phe Leu Asn Arg Tyr Arg Tyr Thr Leu Glu Lys Ala Gly
                565                 570                 575

Glu Tyr Leu Val Arg Leu Arg Tyr Ala Ala Asp Ala Asp Ile Val Leu
            580                 585                 590

Tyr Val Gly Gly Val Lys Ile Gln Met Pro Lys Thr Met Asn Pro Gly
        595                 600                 605

Glu Asp Leu Thr Phe Lys Thr Phe Lys Val Ala Ala Ala Asn Ser Thr
    610                 615                 620

Leu Asn Leu Leu Glu Asn Gly Ser Leu Ala Leu Gln Tyr Leu Tyr Leu
625                 630                 635                 640

Asn Asp Pro Asn Ser Thr Leu Ala Gly Thr Val Tyr Val Asp Arg Ile
                645                 650                 655

Glu Phe Ala Pro Ala Asp Glu Thr Tyr Glu Ala Glu Gln Asp Leu Glu
            660                 665                 670

Ala Ala Lys Lys Ala Val Asn Ala Leu Phe Thr Asn Thr Lys Asp Gly
        675                 680                 685

Leu Arg Pro Gly Val Thr Asp Tyr Glu Val Asn Gln Ala Ala Asn Leu
    690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Glu Ala Arg Asn Leu
                725                 730                 735

Leu Gln Asp Pro Asp Phe Gln Glu Ile Asn Gly Glu Asn Gly Trp Thr
            740                 745                 750

Gly Ser Thr Gly Ile Glu Ile Gly Glu Gly Asp Ala Val Phe Lys Gly
        755                 760                 765

Arg Tyr Leu Ser Leu Pro Gly Ala Arg Glu Ile Asp Thr Glu Thr Tyr
    770                 775                 780

Pro Thr Tyr Leu Tyr Gln Lys Ile Glu Val Ser Arg Leu Lys Pro Tyr
785                 790                 795                 800

Thr Arg Tyr Arg Leu Lys Gly Phe Val Gly Ser Ser Gln Gly Leu Glu
                805                 810                 815

Ile Tyr Thr Ile His His Gln Thr Asn Arg Ile Val Lys Asn Val Pro
            820                 825                 830
```

Asn Asp Leu Gln Pro Asp Val Ser Pro Val Asn Ala Asp Gly Ser Ile
    835                 840                 845

Asn Arg Cys Ser Glu Gln Lys Tyr Val Asn Ser Arg Leu Lys Ile Glu
    850                 855                 860

Asn Arg Ser Gly Asp Ala His Glu Phe Ser Ile Pro Ile Asp Thr Gly
865                 870                 875                 880

Glu Ile Asp Tyr Asn Glu Asn Ala Gly Ile Trp Val Gly Phe Lys Ile
                885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
            915                 920                 925

Gln Gln Trp Lys Ile Gln Met Thr Arg Arg Glu Glu Thr Asp Arg
    930                 935                 940

Arg Tyr Met Ala Ser Lys Gln Ala Val Asp Arg Leu Tyr Val Asp Tyr
945                 950                 955                 960

Gln Asp Gln Gln Leu Asn Pro Val Val Glu Ile Thr Asp Leu Thr Ala
                965                 970                 975

Ala Gln Asn Leu Ile Gln Ser Ile Pro Tyr Val Tyr Asn Glu Met Phe
            980                 985                 990

Pro Glu Ile Pro Gly Met Asn Tyr Thr Lys Phe Thr Glu Leu Thr Asp
            995                 1000                1005

Arg Leu Gln Gln Ala Tyr Ser Leu Tyr Asp Gln Arg Asn Ala Ile
    1010                1015                1020

Pro Asn Gly Asp Phe Arg Asn Gly Leu Ser Asn Trp Asn Ala Thr
    1025                1030                1035

Pro Gly Val Asp Ile Gln Gln Ile Asn Asn Thr Ser Val Leu Val
    1040                1045                1050

Ile Pro Asn Trp Asp Glu Val Ser Gln Gln Phe Thr Val Gln
    1055                1060                1065

Pro Asn Gln Arg Tyr Val Leu Arg Val Thr Ala Arg Lys Glu Gly
    1070                1075                1080

Ile Gly Asn Gly Tyr Val Ser Ile Arg Asp Gly Gly Asn Gln Thr
    1085                1090                1095

Glu Thr Leu Thr Phe Asn Ala Asn Glu Tyr Asp Thr Asn Gly Val
    1100                1105                1110

Tyr Asn Asp Gln Thr Gly Tyr Ile Thr Lys Thr Val Thr Phe Ile
    1115                1120                1125

Pro Tyr Thr Asp Gln Met Trp Ile Glu Ile Ser Glu Thr Glu Gly
    1130                1135                1140

Met Phe Tyr Ile Glu Ser Val Glu Leu Ile Val Asp Val Glu
    1145                1150                1155

<210> SEQ ID NO 3
<211> LENGTH: 1992
<212> TYPE: DNA
<213> ORGANISM: Bacillus thuringiensis

<400> SEQUENCE: 3
atgagtccaa ataatcaaaa tgaatatgaa attatagatg cgacaccttc tacttctgta      60
tccaataatt ctaacagata cccttttgcg aatgagtcaa caaatgcgtt acaaaatatg     120
aattataaag attatttaag aatgtctggg ggaaatgcta gtgaatatcc tggttcacct     180
gaggcattta taagcgagca ggatgcagct aaggccgcaa ttgatctaat aggtacatta     240

```
ctaacagggt taggactgcc gtttgttggg ccgatagtgg gtctttatac tcaacttatt    300
gatattctgt ggccttcagg ggaaaagagt caatgggaaa tttttatgga acaagtagaa    360
gtactcgtta atcagagaat agaagaggcc gtaaagagta aggcgattgc ggaattagaa    420
gggttaggaa acaacttcca attatatcta acggcacttg aagaatggca agaaaaccca    480
aatggtgcaa gagctttacg agatgttcga aatcgatttg aaatcctgga tagtttattt    540
acgcaatata tgccatcttt tcgagtggca aaatttgaag taccgcttct tatagtatat    600
acaatggcag caaaccttca tttactttta ttaaaggacg catcaatttt tggagaagaa    660
tggggattgt caacaactac tattaataac tattatgatc gtcaaatgaa acttaccgca    720
gaatattctg attattgtgt aaagtggtat aaaactggtt tacaaaaatt aattggcgtg    780
agcgctaaac aatgggtagc atataatcgt ttccgtagag aaatgacatt ggcggtgtta    840
gatcttgtgt cgttatttcc aaactatgac gcgcgtacgt atccaattca aacgaaagcc    900
caacttacaa gggaattgta tacagatcca ctgggtgcgg taaatgtgcc ttcaattggt    960
tcctggtatg acaaagcacc ttctttcgga gtgatagaag catccgttat tcgaccaccc   1020
catgtatttg attttataac aggactcaca gtgtatacac aatcacgtag cgtttctacc   1080
gctcattata taagacattg ggctggtcat aaaatacgct atcgtcggac tctggatgtt   1140
aataataatg aacagatgta tggaactaat gaaaatctac acagcactag tgtgtatgat   1200
tttacggatt atgatattta caagacgtta tcaaagatg cggtgctctt tgatattgtt    1260
ttccctgttg gtacgtatat attttttgga atgccagaag tcgagttttt catggtaaac   1320
caattgaata ataccagaaa gacgttaacg tataaaccag gttccaaaga tattatagag   1380
cggacaagag attcggaatt agaattgcct ccagaaactt cagatcaacc aaattatgag   1440
tcatatagcc atagattatg tcatatcaca agtattcccg cgacgggttc aactaccgga   1500
ttagtacctg tgtttttcttg gacacatcga agtgcagatt taaacaatac aatatattca   1560
gataaaatca ctcaaattcc ggctgttaaa agttgggact attctagtcc tggttcttat   1620
ataaagggac caggacatac aggaggagat ttactacagt atataagaag gggttctgca   1680
ggagggcttt tcctaaatcg atataggtat acattagaaa aagcagggga atatcttgta   1740
aggttgaggt atgctgctga tgcagatatt gtattgtatg taggcggtgt taagattcag   1800
atgccaaaaa caatgaaccc aggtgaggat ctaacatttta aaacttttaa agttgcagca   1860
gctaatagta ccttgaattt attagagaat ggaagtcttg cgttgcaata tttatattta   1920
aatgatccta attctacatt ggctggtacc gtttatgttg atcgaatcga attcgcccca   1980
gcagatgaga ca                                                        1992
```

<210> SEQ ID NO 4
<211> LENGTH: 2001
<212> TYPE: DNA
<213> ORGANISM: Artificial Sequence
<220> FEATURE:
<223> OTHER INFORMATION: Maize optimized

<400> SEQUENCE: 4

```
atgtcccta acaaccagaa tgagtacgag atcattgatg cgacaccatc aacctcggtg     60
agcaacaact cgaaccgcta tccgtttgcg aacgagtcta caaatgcgct gcaaaacatg    120
aactacaagg actatctgcg gatgtctgga ggcaacgcct ctgagtaccc tggctcaccc    180
gaggccttca tcagcgaaca agacgctgcc aaggcagcta tcgatctgat cgggacgctg    240
```

```
ctgactggcc tcggactccc ctttgtggga cctatcgtgg ggttgtacac ccagctgatc    300
gacatccttt ggccttccgg tgaaaagtca cagtgggaaa tcttcatgga caagttgag    360 gttctcgtca atcagaggat tgaggaggct gtgaagtcca aggccattgc cgagcttgaa    420
ggcctgggca caacttcca gctctatctc accgctcttg aggaatggca agaaaacccc    480
aacggtgcta gggctttgag gacgtcaga atcgctttg aaatcctcga ctcactgttc    540
acgcagtaca tgccctcctt cgcgtcgcg aagtttgagg tgccactctt gattgtctac    600
acaatggctg ctaaccttca ccttctgctc ttgaaagatg cgtcgatctt tggtgaggaa    660
tggggactct caacgaccac gatcaacaac tactacgata gcagatgaa gctgactgcg    720 gagtacagcg attactgcgt caagtggtac aagaccggac tccagaaact gatcggtgtt    780
tccgcaaagc agtgggtcgc ctacaatcgg tttaggagag agatgacgct cgctgttctg    840
gaccttgttt cactgttccc gaactacgac gcgaggactt atcctataca aacgaaggca    900
cagctgacca gagagcttta caccgaccca cttggagccg tgaacgtccc atccattggc    960
agctggtatg acaaagctcc ctcctttggc gtgatcgagg cctcagtgat aaggcctccg    1020
catgtgttcg acttcatcac tggcttgaca gtttacaccc agtcgaggag cgtctctaca    1080
gcgcactaca tacgccattg ggctggccac aagattagat atcggaggac cctcgacgtc    1140
aacaacaatg agcagatgta cggcaccaat gagaatctcc actcaacatc tgtctacgat    1200
ttcaccgact acgatatcta caagacactg tccaaggatg cagttttgtt tgacattgtg    1260
ttcccagttg gcacctacat cttctttggg atgccagagg tggagttctt catggtcaac    1320
cagctgaaca acacacgcaa gaccctcacc tacaaacctg ggtcgaagga catcattgag    1380
cggacacgcg actcggaatt ggagctgcct ccggagactt cagaccagcc taactacgaa    1440
agctactccc cagactgtg tcatatcacc tccatcccag caactggttc caccactggc    1500
ttggtcccag tgttctcttg gacgcatcgc agcgctgacc ttaacaatac gatctactcg    1560
gataagatca ctcagatccc agccgtgaag agctgggatt actcaagccc tggcagctac    1620
atcaaaggtc ctggccacac gggagggat cttctccagt acattcggag gggttccgct    1680
ggaggtgcct tcctcaacag atatcgctac acccttgaga aggctggcga gtatctcgtg    1740
aggctcagat atgcagccga tgccgacatt gtcctctacg ttggaggggt caagatacaa    1800
atgcctaaga ccatgaatcc tggtgaggac ttgaccttca aaacgttcaa ggtggcagca    1860
gcgaactcta cgttgaatct tctggaaaac ggctcactcg ccttgcagta tctctatctg    1920
aatgacccta cagcacgct tgctggcact gtgtacgtgg acagaattga gttcgctcca    1980
gcagatgaga ctctcgagtg a                                             2001
```

<210> SEQ ID NO 5
<211> LENGTH: 666
<212> TYPE: PRT
<213> ORGANISM: Bacillus thuringiensis

<400> SEQUENCE: 5

```
Met Ser Pro Asn Asn Gln Asn Glu Tyr Glu Ile Ile Asp Ala Thr Pro
1               5                   10                  15

Ser Thr Ser Val Ser Asn Asn Ser Asn Arg Tyr Pro Phe Ala Asn Glu
            20                  25                  30

Ser Thr Asn Ala Leu Gln Asn Met Asn Tyr Lys Asp Tyr Leu Arg Met
        35                  40                  45

Ser Gly Gly Asn Ala Ser Glu Tyr Pro Gly Ser Pro Glu Ala Phe Ile
    50                  55                  60
```

```
Ser Glu Gln Asp Ala Ala Lys Ala Ala Ile Asp Leu Ile Gly Thr Leu
 65                  70                  75                  80

Leu Thr Gly Leu Gly Leu Pro Phe Val Gly Pro Ile Val Gly Leu Tyr
                 85                  90                  95

Thr Gln Leu Ile Asp Ile Leu Trp Pro Ser Gly Glu Lys Ser Gln Trp
            100                 105                 110

Glu Ile Phe Met Glu Gln Val Glu Val Leu Val Asn Gln Arg Ile Glu
            115                 120                 125

Glu Ala Val Lys Ser Lys Ala Ile Ala Glu Leu Glu Gly Leu Gly Asn
            130                 135                 140

Asn Phe Gln Leu Tyr Leu Thr Ala Leu Glu Glu Trp Gln Glu Asn Pro
145                 150                 155                 160

Asn Gly Ala Arg Ala Leu Arg Asp Val Arg Asn Arg Phe Glu Ile Leu
                165                 170                 175

Asp Ser Leu Phe Thr Gln Tyr Met Pro Ser Phe Arg Val Ala Lys Phe
            180                 185                 190

Glu Val Pro Leu Leu Ile Val Tyr Thr Met Ala Ala Asn Leu His Leu
            195                 200                 205

Leu Leu Leu Lys Asp Ala Ser Ile Phe Gly Glu Glu Trp Gly Leu Ser
210                 215                 220

Thr Thr Thr Ile Asn Asn Tyr Tyr Asp Arg Gln Met Lys Leu Thr Ala
225                 230                 235                 240

Glu Tyr Ser Asp Tyr Cys Val Lys Trp Tyr Lys Thr Gly Leu Gln Lys
                245                 250                 255

Leu Ile Gly Val Ser Ala Lys Gln Trp Val Ala Tyr Asn Arg Phe Arg
            260                 265                 270

Arg Glu Met Thr Leu Ala Val Leu Asp Leu Val Ser Leu Phe Pro Asn
            275                 280                 285

Tyr Asp Ala Arg Thr Tyr Pro Ile Gln Thr Lys Ala Gln Leu Thr Arg
290                 295                 300

Glu Leu Tyr Thr Asp Pro Leu Gly Ala Val Asn Val Pro Ser Ile Gly
305                 310                 315                 320

Ser Trp Tyr Asp Lys Ala Pro Ser Phe Gly Val Ile Glu Ala Ser Val
                325                 330                 335

Ile Arg Pro Pro His Val Phe Asp Phe Ile Thr Gly Leu Thr Val Tyr
            340                 345                 350

Thr Gln Ser Arg Ser Val Ser Thr Ala His Tyr Ile Arg His Trp Ala
            355                 360                 365

Gly His Lys Ile Arg Tyr Arg Arg Thr Leu Asp Val Asn Asn Asn Glu
            370                 375                 380

Gln Met Tyr Gly Thr Asn Glu Asn Leu His Ser Thr Ser Val Tyr Asp
385                 390                 395                 400

Phe Thr Asp Tyr Asp Ile Tyr Lys Thr Leu Ser Lys Asp Ala Val Leu
                405                 410                 415

Phe Asp Ile Val Phe Pro Val Gly Thr Tyr Ile Phe Gly Met Pro
            420                 425                 430

Glu Val Glu Phe Phe Met Val Asn Gln Leu Asn Asn Thr Arg Lys Thr
            435                 440                 445

Leu Thr Tyr Lys Pro Gly Ser Lys Asp Ile Ile Glu Arg Thr Arg Asp
            450                 455                 460

Ser Glu Leu Glu Leu Pro Pro Glu Thr Ser Asp Gln Pro Asn Tyr Glu
465                 470                 475                 480
```

```
Ser Tyr Ser His Arg Leu Cys His Ile Thr Ser Ile Pro Ala Thr Gly
            485                 490                 495

Ser Thr Thr Gly Leu Val Pro Val Phe Ser Trp Thr His Arg Ser Ala
        500                 505                 510

Asp Leu Asn Asn Thr Ile Tyr Ser Asp Lys Ile Thr Gln Ile Pro Ala
        515                 520                 525

Val Lys Ser Trp Asp Tyr Ser Ser Pro Gly Ser Tyr Ile Lys Gly Pro
    530                 535                 540

Gly His Thr Gly Gly Asp Leu Leu Gln Tyr Ile Arg Arg Gly Ser Ala
545                 550                 555                 560

Gly Gly Ala Phe Leu Asn Arg Tyr Arg Tyr Thr Leu Glu Lys Ala Gly
                565                 570                 575

Glu Tyr Leu Val Arg Leu Arg Tyr Ala Ala Asp Ala Asp Ile Val Leu
            580                 585                 590

Tyr Val Gly Gly Val Lys Ile Gln Met Pro Lys Thr Met Asn Pro Gly
        595                 600                 605

Glu Asp Leu Thr Phe Lys Thr Phe Lys Val Ala Ala Ala Asn Ser Thr
    610                 615                 620

Leu Asn Leu Leu Glu Asn Gly Ser Leu Ala Leu Gln Tyr Leu Tyr Leu
625                 630                 635                 640

Asn Asp Pro Asn Ser Thr Leu Ala Gly Thr Val Tyr Val Asp Arg Ile
                645                 650                 655

Glu Phe Ala Pro Ala Asp Glu Thr Tyr Glu
            660                 665

<210> SEQ ID NO 6
<211> LENGTH: 3630
<212> TYPE: DNA
<213> ORGANISM: Artificial Sequence
<220> FEATURE:
<223> OTHER INFORMATION: Maize optimized

<400> SEQUENCE: 6 atgtcccta caaccagaa tgagtacgag atcattgatg cgacaccatc aacctcggtg      60
agcaacaact cgaaccgcta tccgtttgcg aacgagtcta caaatgcgct gcaaaacatg     120
aactacaagg actatctgcg gatgtctgga ggcaacgcct ctgagtaccc tggctcaccc     180
gaggccttca tcagcgaaca agacgctgcc aaggcagcta tcgatctgat cgggacgctg     240
ctgactggcc tcggactccc ctttgtggga cctatcgtgg ggttgtacac ccagctgatc     300
gacatccttt ggccttccgg tgaaaagtca cagtgggaaa tcttcatgga caagttgag      360 gttctcgtca atcagaggat tgaggaggct gtgaagtcca aggccattgc cgagcttgaa     420
ggcctgggca caacttcca gctctatctc accgctcttg aggaatggca agaaaacccc     480
aacggtgcta gggctttgag gacgtcaga atcgctttg aaatcctcga ctcactgttc      540
acgcagtaca tgcctccctt cgcgtcgcg aagtttgagg tgccactctt gattgtctac     600
acaatggctg ctaaccttca ccttctgctc ttgaaagatg cgtcgatctt tggtgaggaa     660
tggggactct caacgaccac gatcaacaac tactacgata ggcagatgaa gctgactgcg     720
gagtacagcg attactgcgt caagtggtac aagaccggac tccagaaact gatcggtgtt     780
tccgcaaagc agtgggtcgc ctacaatcgg tttaggagag agatgacgct cgctgttctg     840
gaccttgttt cactgttccc gaactacgac gcgaggactt atcctataca aacgaaggca     900
cagctgacca gagagcttta caccgaccca cttggagccg tgaacgtccc atccattggc     960
agctggtatg acaaagctcc ctcctttggc gtgatcgagg cctcagtgat aaggcctccg    1020
```

```
catgtgttcg acttcatcac tggcttgaca gtttacaccc agtcgaggag cgtctctaca    1080
gcgcactaca tacgccattg ggctggccac aagattagat atcggaggac cctcgacgtc    1140
aacaacaatg agcagatgta cggcaccaat gagaatctcc actcaacatc tgtctacgat    1200
ttcaccgact acgatatcta caagacactg tccaaggatg cagttttgtt tgacattgtg    1260
ttcccagttg gcacctacat cttctttggg atgccagagg tggagttctt catggtcaac    1320
cagctgaaca acacacgcaa gaccctcacc tacaaacctg ggtcgaagga catcattgag    1380
cggacacgcg actcggaatt ggagctgcct ccggagactt cagaccagcc taactacgaa    1440
agctactccc acagactgtg tcatatcacc tccatcccag caactggttc caccactggc    1500
ttggtcccag tgttctcttg gacgcatcgc agcgctgacc ttaacaatac gatctactcg    1560
gataagatca ctcagatccc agccgtgaag agctgggatt actcaagccc tggcagctac    1620
atcaaaggtc ctggccacac gggaggggat cttctccagt acattcggag gggttccgct    1680
ggaggtgcct tcctcaacag atatcgctac acccttgaga aggctggcga gtatctcgtg    1740
aggctcagat atgcagccga tgccgacatt gtcctctacg ttggaggggt caagatacaa    1800
atgcctaaga ccatgaatcc tggtgaggac ttgaccttca aaacgttcaa ggtggcagca    1860
gcgaactcta cgttgaatct tctggaaaac ggctcactcg ccttgcagta tctctatctg    1920
aatgacccta acagcacgct tgctggcact gtgtacgtgg acagaattga gttcgctcca    1980
gcagatgaga ctctcgaggc tgaatcggat cttgaaaggg cacagaaggc agtcaacgct    2040
ctcttcacca gctcaaatca gattggcctt aagaccgatg ttactgacta tcatatcgac    2100
agagtttcta accttgtcga gtgcctctcc gacgagttct gtctcgacga aaagaaggaa    2160
ctctccgaga aagtgaagca cgcgaaacgc ctctcggatg aacggaactt gctgcaagat    2220
ccgaacttca gaggcatcaa tcgccagttg gatagaggct ggaggggatc aaccgacata    2280
accattcaag gtggggatga tgtgttcaag gaaaactacg tgacattgct gggcaccttc    2340
gacgagtgct atcccacgta tctctatcag aagattgacg agtccaagct caaagcctac    2400
acacgctatc agctcagagg ctacattgag gactctcaag acctcgaaat ctacttgatc    2460
agatacaacg ccaagcacga gacggtgaac gtccctggga ctgggtcact gtggccactg    2520
tcggcaccct cgccaatcgg aaagtgcgct caccacagcc accacttctc ccttgacata    2580
gatgttgggt gtacggactt gaatgaggat ctgggtgtgt gggtgatctt aagatcaag    2640 acccaagatg gtcatgcgag gcttggcaac cttgagttcc ttgaagagaa gcctttggtc    2700
ggagaggcac tggctcgcgt gaagagggct gagaagaaat ggagggacaa gagggagaaa    2760
ctggagtggg agaccaacat agtgtacaag gaggccaagg agtcagtgga cgcactgttt    2820
gtcaattccc agtatgatag gctccaagcg gacacgaaca tcgccatgat ccatgcagcg    2880
gacaagaggg ttcactccat aagggaggcc tatcttccgg agctgtcagt gattcctggg    2940
gtcaacgcag ccatctttga ggaattggaa gggaggatct tcaccgcttt ctctctgtac    3000
gacgctcgga acgtcatcaa gaatggtgat ttcaacaatg gactcagctg ctggaacgtg    3060
aaagggcatg tcgatgttga agaacagaac aatcaccgca gcgtgctggt ggttccggag    3120
tgggaagccg aggtctcaca agaagtcaga gtgtgccctg ggagggggtta catcttgcgg    3180 gtcacagcct acaaggaagg ttatggcgaa ggctgtgtca cgatccatga gatcgaaaac    3240
aacacagacg agctgaagtt ttccaactgt gttgaggagg aggtctatcc taacaatact    3300
gttacgtgca acgactacac agccactcaa gaggagtacg agggcactta cacctctcgc    3360
```

```
aacagaggct acgacggtgc ctacgagtca acagctccg tgccagcgga ctacgcctcg    3420
gcttacgaag agaaggcgta caccgacggt cggagggata acccgtgcga gagcaataga    3480
ggctatggcg actacactcc tctcccagct ggctacgtga ccaaggagtt ggagtacttt    3540
ccggagacag acaaagtctg gattgagatt ggagagacag aaggcacgtt catcgtggac    3600
tctgttgaac tcttgctgat ggaggagtga                                     3630
```

<210> SEQ ID NO 7
<211> LENGTH: 1209
<212> TYPE: PRT
<213> ORGANISM: Artificial Sequence
<220> FEATURE:
<223> OTHER INFORMATION: chimeric sequence

<400> SEQUENCE: 7

```
Met Ser Pro Asn Asn Gln Asn Glu Tyr Glu Ile Ile Asp Ala Thr Pro
1               5                   10                  15

Ser Thr Ser Val Ser Asn Asn Ser Asn Arg Tyr Pro Phe Ala Asn Glu
            20                  25                  30

Ser Thr Asn Ala Leu Gln Asn Met Asn Tyr Lys Asp Tyr Leu Arg Met
        35                  40                  45

Ser Gly Gly Asn Ala Ser Glu Tyr Pro Gly Ser Pro Glu Ala Phe Ile
    50                  55                  60

Ser Glu Gln Asp Ala Ala Lys Ala Ala Ile Asp Leu Ile Gly Thr Leu
65                  70                  75                  80

Leu Thr Gly Leu Gly Leu Pro Phe Val Gly Pro Ile Val Gly Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Val Leu Val Asn Gln Arg Ile Glu
        115                 120                 125

Glu Ala Val Lys Ser Lys Ala Ile Ala Glu Leu Glu Gly Leu Gly Asn
    130                 135                 140

Asn Phe Gln Leu Tyr Leu Thr Ala Leu Glu Glu Trp Gln Glu Asn Pro
145                 150                 155                 160

Asn Gly Ala Arg Ala Leu Arg Asp Val Arg Asn Arg Phe Glu Ile Leu
                165                 170                 175

Asp Ser Leu Phe Thr Gln Tyr Met Pro Ser Phe Arg Val Ala Lys Phe
            180                 185                 190

Glu Val Pro Leu Leu Ile Val Tyr Thr Met Ala Ala Asn Leu His Leu
        195                 200                 205

Leu Leu Leu Lys Asp Ala Ser Ile Phe Gly Glu Glu Trp Gly Leu Ser
    210                 215                 220

Thr Thr Thr Ile Asn Asn Tyr Tyr Asp Arg Gln Met Lys Leu Thr Ala
225                 230                 235                 240

Glu Tyr Ser Asp Tyr Cys Val Lys Trp Tyr Lys Thr Gly Leu Gln Lys
                245                 250                 255

Leu Ile Gly Val Ser Ala Lys Gln Trp Val Ala Tyr Asn Arg Phe Arg
            260                 265                 270

Arg Glu Met Thr Leu Ala Val Leu Asp Leu Val Ser Leu Phe Pro Asn
        275                 280                 285

Tyr Asp Ala Arg Thr Tyr Pro Ile Gln Thr Lys Ala Gln Leu Thr Arg
    290                 295                 300

Glu Leu Tyr Thr Asp Pro Leu Gly Ala Val Asn Val Pro Ser Ile Gly
305                 310                 315                 320
```

-continued

Ser Trp Tyr Asp Lys Ala Pro Ser Phe Gly Val Ile Glu Ala Ser Val
            325                 330                 335

Ile Arg Pro Pro His Val Phe Asp Phe Ile Thr Gly Leu Thr Val Tyr
            340                 345                 350

Thr Gln Ser Arg Ser Val Ser Thr Ala His Tyr Ile Arg His Trp Ala
            355                 360                 365

Gly His Lys Ile Arg Tyr Arg Arg Thr Leu Asp Val Asn Asn Asn Glu
        370                 375                 380

Gln Met Tyr Gly Thr Asn Glu Asn Leu His Ser Thr Ser Val Tyr Asp
385                 390                 395                 400

Phe Thr Asp Tyr Asp Ile Tyr Lys Thr Leu Ser Lys Asp Ala Val Leu
                405                 410                 415

Phe Asp Ile Val Phe Pro Val Gly Thr Tyr Ile Phe Phe Gly Met Pro
                420                 425                 430

Glu Val Glu Phe Phe Met Val Asn Gln Leu Asn Asn Thr Arg Lys Thr
                435                 440                 445

Leu Thr Tyr Lys Pro Gly Ser Lys Asp Ile Ile Glu Arg Thr Arg Asp
        450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
                500                 505                 510

Asp Leu Asn Asn Thr Ile Tyr Ser Asp Lys Ile Thr Gln Ile Pro Ala
                515                 520                 525

Val Lys Ser Trp Asp Tyr Ser Ser Pro Gly Ser Tyr Ile Lys Gly Pro
        530                 535                 540

Gly His Thr Gly Gly Asp Leu Leu Gln Tyr Ile Arg Arg Gly Ser Ala
545                 550                 555                 560

Gly Gly Ala Phe Leu Asn Arg Tyr Arg Tyr Thr Leu Glu Lys Ala Gly
                565                 570                 575

Glu Tyr Leu Val Arg Leu Arg Tyr Ala Ala Asp Ala Asp Ile Val Leu
                580                 585                 590

Tyr Val Gly Gly Val Lys Ile Gln Met Pro Lys Thr Met Asn Pro Gly
        595                 600                 605

Glu Asp Leu Thr Phe Lys Thr Phe Lys Val Ala Ala Ala Asn Ser Thr
        610                 615                 620

Leu Asn Leu Leu Glu Asn Gly Ser Leu Ala Leu Gln Tyr Leu Tyr Leu
625                 630                 635                 640

Asn Asp Pro Asn Ser Thr Leu Ala Gly Thr Val Tyr Val Asp Arg Ile
                645                 650                 655

Glu Phe Ala Pro Ala Asp Glu Thr Leu Glu Ala Glu Ser Asp Leu Glu
                660                 665                 670

Arg Ala Gln Lys Ala Val Asn Ala Leu Phe Thr Ser Ser Asn Gln Ile
        675                 680                 685

Gly Leu Lys Thr Asp Val Thr Asp Tyr His Ile Asp Arg Val Ser Asn
        690                 695                 700

Leu Val Glu Cys Leu Ser Asp Glu Phe Cys Leu Asp Glu Lys Lys Glu
705                 710                 715                 720

Leu Ser Glu Lys Val Lys His Ala Lys Arg Leu Ser Asp Glu Arg Asn
                725                 730                 735

```
Leu Leu Gln Asp Pro Asn Phe Arg Gly Ile Asn Arg Gln Leu Asp Arg
            740                 745                 750

Gly Trp Arg Gly Ser Thr Asp Ile Thr Ile Gln Gly Gly Asp Asp Val
            755                 760                 765

Phe Lys Glu Asn Tyr Val Thr Leu Leu Gly Thr Phe Asp Glu Cys Tyr
            770                 775                 780

Pro Thr Tyr Leu Tyr Gln Lys Ile Asp Glu Ser Lys Leu Lys Ala Tyr
785                 790                 795                 800

Thr Arg Tyr Gln Leu Arg Gly Tyr Ile Glu Asp Ser Gln Asp Leu Glu
                805                 810                 815

Ile Tyr Leu Ile Arg Tyr Asn Ala Lys His Glu Thr Val Asn Val Pro
            820                 825                 830

Gly Thr Gly Ser Leu Trp Pro Leu Ser Ala Pro Ser Pro Ile Gly Lys
            835                 840                 845

Cys Ala His His Ser His His Phe Ser Leu Asp Ile Asp Val Gly Cys
            850                 855                 860

Thr Asp Leu Asn Glu Asp Leu Gly Val Trp Val Ile Phe Lys Ile Lys
865                 870                 875                 880

Thr Gln Asp Gly His Ala Arg Leu Gly Asn Leu Glu Phe Leu Glu Glu
                885                 890                 895

Lys Pro Leu Val Gly Glu Ala Leu Ala Arg Val Lys Arg Ala Glu Lys
            900                 905                 910

Lys Trp Arg Asp Lys Arg Glu Lys Leu Glu Trp Glu Thr Asn Ile Val
            915                 920                 925

Tyr Lys Glu Ala Lys Glu Ser Val Asp Ala Leu Phe Val Asn Ser Gln
            930                 935                 940

Tyr Asp Arg Leu Gln Ala Asp Thr Asn Ile Ala Met Ile His Ala Ala
945                 950                 955                 960

Asp Lys Arg Val His Ser Ile Arg Glu Ala Tyr Leu Pro Glu Leu Ser
                965                 970                 975

Val Ile Pro Gly Val Asn Ala Ala Ile Phe Glu Glu Leu Glu Gly Arg
            980                 985                 990

Ile Phe Thr Ala Phe Ser Leu Tyr Asp Ala Arg Asn Val Ile Lys Asn
            995                 1000                1005

Gly Asp Phe Asn Asn Gly Leu Ser Cys Trp Asn Val Lys Gly His
            1010                1015                1020

Val Asp Val Glu Glu Gln Asn Asn His Arg Ser Val Leu Val Val
            1025                1030                1035

Pro Glu Trp Glu Ala Glu Val Ser Gln Glu Val Arg Val Cys Pro
            1040                1045                1050

Gly Arg Gly Tyr Ile Leu Arg Val Thr Ala Tyr Lys Glu Gly Tyr
            1055                1060                1065

Gly Glu Gly Cys Val Thr Ile His Glu Ile Glu Asn Asn Thr Asp
            1070                1075                1080

Glu Leu Lys Phe Ser Asn Cys Val Glu Glu Glu Val Tyr Pro Asn
            1085                1090                1095

Asn Thr Val Thr Cys Asn Asp Tyr Thr Ala Thr Gln Glu Glu Tyr
            1100                1105                1110

Glu Gly Thr Tyr Thr Ser Arg Asn Arg Gly Tyr Asp Gly Ala Tyr
            1115                1120                1125

Glu Ser Asn Ser Ser Val Pro Ala Asp Tyr Ala Ser Ala Tyr Glu
            1130                1135                1140

Glu Lys Ala Tyr Thr Asp Gly Arg Arg Asp Asn Pro Cys Glu Ser
```

```
                     1145                1150                1155

Asn Arg Gly Tyr Gly Asp Tyr Thr Pro Leu Pro Ala Gly Tyr Val
            1160                1165                1170

Thr Lys Glu Leu Glu Tyr Phe Pro Glu Thr Asp Lys Val Trp Ile
        1175                1180                1185

Glu Ile Gly Glu Thr Glu Gly Thr Phe Ile Val Asp Ser Val Glu
    1190                1195                1200

Leu Leu Leu Met Glu Glu
    1205

<210> SEQ ID NO 8
<211> LENGTH: 666
<212> TYPE: PRT
<213> ORGANISM: Artificial Sequence
<220> FEATURE:
<223> OTHER INFORMATION: Maize optimized

<400> SEQUENCE: 8

Met Ser Pro Asn Gln Asn Glu Tyr Glu Ile Ile Asp Ala Thr Pro
1               5                   10                  15

Ser Thr Ser Val Ser Asn Asn Ser Asn Arg Tyr Pro Phe Ala Asn Glu
            20                  25                  30

Ser Thr Asn Ala Leu Gln Asn Met Asn Tyr Lys Asp Tyr Leu Arg Met
        35                  40                  45

Ser Gly Gly Asn Ala Ser Glu Tyr Pro Gly Ser Pro Glu Ala Phe Ile
    50                  55                  60

Ser Glu Gln Asp Ala Ala Lys Ala Ala Ile Asp Leu Ile Gly Thr Leu
65                  70                  75                  80

Leu Thr Gly Leu Gly Leu Pro Phe Val Gly Pro Ile Val Gly Leu Tyr
                85                  90                  95

Thr Gln Leu Ile Asp Ile Leu Trp Pro Ser Gly Glu Lys Ser Gln Trp
            100                 105                 110

Glu Ile Phe Met Glu Gln Val Glu Val Leu Val Asn Gln Arg Ile Glu
        115                 120                 125

Glu Ala Val Lys Ser Lys Ala Ile Ala Glu Leu Glu Gly Leu Gly Asn
    130                 135                 140

Asn Phe Gln Leu Tyr Leu Thr Ala Leu Glu Glu Trp Gln Glu Asn Pro
145                 150                 155                 160

Asn Gly Ala Arg Ala Leu Arg Asp Val Arg Asn Arg Phe Glu Ile Leu
                165                 170                 175

Asp Ser Leu Phe Thr Gln Tyr Met Pro Ser Phe Arg Val Ala Lys Phe
            180                 185                 190

Glu Val Pro Leu Leu Ile Val Tyr Thr Met Ala Ala Asn Leu His Leu
        195                 200                 205

Leu Leu Leu Lys Asp Ala Ser Ile Phe Gly Glu Glu Trp Gly Leu Ser
    210                 215                 220

Thr Thr Thr Ile Asn Asn Tyr Tyr Asp Arg Gln Met Lys Leu Thr Ala
225                 230                 235                 240

Glu Tyr Ser Asp Tyr Cys Val Lys Trp Tyr Lys Thr Gly Leu Gln Lys
                245                 250                 255

Leu Ile Gly Val Ser Ala Lys Gln Trp Val Ala Tyr Asn Arg Phe Arg
            260                 265                 270

Arg Glu Met Thr Leu Ala Val Leu Asp Leu Val Ser Leu Phe Pro Asn
        275                 280                 285

Tyr Asp Ala Arg Thr Tyr Pro Ile Gln Thr Lys Ala Gln Leu Thr Arg
```

```
            290              295             300
Glu Leu Tyr Thr Asp Pro Leu Gly Ala Val Asn Val Pro Ser Ile Gly
305                 310                 315                 320

Ser Trp Tyr Asp Lys Ala Pro Ser Phe Gly Val Ile Glu Ala Ser Val
                325                 330                 335

Ile Arg Pro Pro His Val Phe Asp Phe Ile Thr Gly Leu Thr Val Tyr
            340                 345                 350

Thr Gln Ser Arg Ser Val Ser Thr Ala His Tyr Ile Arg His Trp Ala
        355                 360                 365

Gly His Lys Ile Arg Tyr Arg Arg Thr Leu Asp Val Asn Asn Asn Glu
    370                 375                 380

Gln Met Tyr Gly Thr Asn Glu Asn Leu His Ser Thr Ser Val Tyr Asp
385                 390                 395                 400

Phe Thr Asp Tyr Asp Ile Tyr Lys Thr Leu Ser Lys Asp Ala Val Leu
                405                 410                 415

Phe Asp Ile Val Phe Pro Val Gly Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Thr Tyr Lys Pro Gly Ser Lys Asp Ile Ile Glu Arg Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Asn Asn Thr Ile Tyr Ser Asp Lys Ile Thr Gln Ile Pro Ala
        515                 520                 525

Val Lys Ser Trp Asp Tyr Ser Ser Pro Gly Ser Tyr Ile Lys Gly Pro
    530                 535                 540

Gly His Thr Gly Gly Asp Leu Leu Gln Tyr Ile Arg Arg Gly Ser Ala
545                 550                 555                 560

Gly Gly Ala Phe Leu Asn Arg Tyr Arg Tyr Thr Leu Glu Lys Ala Gly
                565                 570                 575

Glu Tyr Leu Val Arg Leu Arg Tyr Ala Ala Asp Ala Asp Ile Val Leu
            580                 585                 590

Tyr Val Gly Gly Val Lys Ile Gln Met Pro Lys Thr Met Asn Pro Gly
        595                 600                 605

Glu Asp Leu Thr Phe Lys Thr Phe Lys Val Ala Ala Ala Asn Ser Thr
    610                 615                 620

Leu Asn Leu Leu Glu Asn Gly Ser Leu Ala Leu Gln Tyr Leu Tyr Leu
625                 630                 635                 640

Asn Asp Pro Asn Ser Thr Leu Ala Gly Thr Val Tyr Val Asp Arg Ile
                645                 650                 655

Glu Phe Ala Pro Ala Asp Glu Thr Leu Glu
            660                 665
```

DIG-17 INSECTICIDAL CRY TOXINS

CROSS-REFERENCE TO RELATED APPLICATIONS

The present application claims priority to U.S. Provisional Application No. 62/043,059, filed Aug. 28, 2014, which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "68466-US-NP_20150820_Seq_Listing_DIG17_ST25.txt", created on Aug. 20, 2015, and having a size of 47 kilobytes, and is filed concurrently with the specification. The sequence listing contained in this ASCII formatted document is part of the specification, and is incorporated herein by reference in its entirety.

BACKGROUND OF THE INVENTION

*Bacillus thuringiensis* (B.t.) is a soil-borne bacterium that produces pesticidal crystal proteins known as delta endotoxins or Cry proteins. Cry proteins are oral intoxicants that function by acting on midgut cells of susceptible insects. Some Cry toxins have been shown to have activity against nematodes. An extensive list of delta endotoxins is maintained and regularly updated at the *Bacillus thuringiensis* Toxin Nomenclature web site maintained by Neil Crickmore. (See Crickmore et al. 1998, page 808).

Coleopterans are a significant group of agricultural pests that cause extensive damage to crops each year. Examples of coleopteran pests include Colorado potato beetle (CPB), corn rootworm, alfalfa weevil, boll weevil, and Japanese beetle. The Colorado potato beetle is an economically important pest that feeds on the leaves of potato, eggplant, tomato, pepper, tobacco, and other plants in the nightshade family. The Colorado potato beetle is a problematic defoliator of potatoes, in part, because it has developed resistance to many classes of insecticides. Cry toxins, including members of the Cry3, Cry7, and Cry8 family members have insecticidal activity against coleopteran insects.

Although production of the currently-deployed Cry proteins in transgenic plants can provide robust protection against the aforementioned pests, thereby protecting grain yield, adult pests have emerged in artificial infestation trials, indicating less than complete larval insect control. Additionally, development of resistant insect populations threatens the long-term durability of Cry proteins in insect pest control. Lepidopteran insects resistant to Cry proteins have developed in the field for *Plutella xylostella* (Tabashnik, 1994), *Trichoplusia ni* (Janmaat and Myers, 2003, 2005), and *Helicoverpa zea* (Tabashnik et al., 2008). Coleopteran insects likewise have developed resistance in the field to Cry proteins (Gassman et al. PLoS ONE July 2011|Volume 6|Issue 7|e22629). Insect resistance to B.t. Cry proteins can develop through several mechanisms (Heckel et al., 2007; Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease.

There is interest in the development of new Cry proteins that provide additional tools for management of coleopteran insect pests. Cry proteins with different modes of action as well as additional Cry transgenic plants can prevent the development of insect resistance and protect the long term utility of B.t. technology for insect pest control.

BRIEF SUMMARY OF THE INVENTION

The present invention is based on the discovery of insecticidal Cry protein toxin designated herein as DIG-17. The invention includes DIG-17, toxin variants of DIG-17, nucleic acids encoding these toxins, methods of controlling pests using these toxins, methods of producing these toxins in transgenic host cells, and transgenic plants that express the toxins. Based on the predicted amino acid sequence of native DIG-17 toxin in SEQ ID NO:2, DIG-17 is classified as belonging to the Cry8 family.

A nucleic acid encoding the DIG-17 protein was discovered and isolated from a B.t. strain internally designated by Dow AgroSciences LLC as PS217U4. The nucleic acid sequence for the full-length coding region was determined, and the full-length protein sequence was deduced from the nucleic acid sequence. A nucleic acid sequence encoding DIG-17 toxin is given in SEQ ID NO:1. A BLAST search using the insecticidal core fragment as a query found that DIG-17 toxin protein has less than 88% sequence identity to the core fragment of the closest Cry toxin known at the time of the search. Thus, DIG-17 represents a new subclass within the Cry8B family of proteins.

The DIG-17 toxins disclosed herein, including variants, can be used alone or in combination with other Cry toxins, such as Cry34Ab1/Cry35Ab1 (DAS-59122-7), Cry3Bb1 (MON88017), Cry3A (MIR604), chimeric Cry3A/Cry1Ab (eCry3.1Ab, FR8A, Event 5307, WO 2008/121633 A1), CryET33 and CryET34, Vip1A, Cry1Ia, CryET84, CryET80, CryET76, CryET71, CryET69, CryET75, CryET39, CryET79, TIC809, TIC810 and CryET74 to control the development of resistant Coleopteran insect populations. Further, DIG-17 toxins can be used alone or in combination with other Cry toxins that control the development of other pest populations, such as, for example, Cry1F, Cry1Ab, Vip Cry2A, Cry1Da, Cry1Ia, and Cry1Ac to control the development of lepidopteran resistant insect populations.

DIG-17 insecticidal toxins may also be used in combination with RNAi methodologies for control of other insect pests. For example, DIG-17 insecticidal toxins can be used in transgenic plants in combination with a dsRNA for suppression of an essential gene in CPB, corn rootworm or another insect pest. Such target genes include, for example, ATPase encoding genes in CPB. Other such target genes include, for example, vacuolar ATPase, ARF-1, Act42A, CHD3, EF-1α, and TFIIB in corn rootworm. An example of a suitable target gene is vacuolar ATPase, as disclosed in WO2007035650.

In one embodiment, the invention provides an isolated, treated, or formulated DIG-17 insecticidal toxin polypeptide comprising a core toxin segment selected from the group consisting of
  (a) the amino acid sequence of residues from approximately 2 to 666 of SEQ ID NO:2;
  (b) an amino acid sequence having at least 80%, 85%, 90%, 91%, 92%, 93%, 94%, 95%, 96%, 97%, 98%, or 99% sequence identity to the amino acid sequence of residues from approximately 2 to 666 of SEQ ID NO:2; and (c) an amino acid sequence of residues from approximately 2 to 666 of SEQ ID NO:2, with up to 20 amino acid substitutions, deletions, or modifications that retain the activity of the toxin of SEQ ID NO:2; or an insecticidal active fragment of either (a), (b) or (c).

In certain embodiments, the DIG-17 insecticidal toxin polypeptide core toxin segment comprises (a') the amino acid sequence of residues from approximately 1 to 666 of SEQ ID NO:2; (b') an amino acid sequence having at least 80%, 85%, 90%, 91%, 92%, 93%, 94%, 95%, 96%, 97%, 98%, or 99% sequence identity to the amino acid sequence of residues from approximately 1 to 666 of SEQ ID NO:2; and (c') an amino acid sequence of residues from approximately 1 to 666 of SEQ ID NO:2, with up to 20 amino acid substitutions, deletions, or modifications that retain the activity of the toxin of SEQ ID NO:2; or an insecticidal active fragment of either (a'), (b') or (c'). In further embodiments, the DIG-17 insecticidal toxin polypeptide of (a), (b), (c), (a'), (b') or (c') can be linked to a C-terminal protoxin, e.g., the C-terminal protoxin of cry1Ab or cry1Ac/cry1Ab chimeric toxin. In related embodiments, the invention provides a recombinant polynucleotide (e.g., a DNA construct) that comprises a nucleotide sequence encoding the DIG-17 insecticidal toxin polypeptide of (a), (b), (c), (a'), (b') or (c') which is operably linked to a heterologous promoter that is not derived from *Bacillus thuringiensis* and is capable of driving expression of the encoded DIG-17 insecticidal toxin polypeptide in a plant. Examples of heterologous promoters are described herein. The invention also provides a transgenic plant that comprises the DNA construct stably incorporated into its genome and a method for protecting a plant from a pest comprising introducing the construct into said plant.

As used herein, each reference to variants or homologs that "retain the activity" of DIG-17 or SEQ ID NO:2 means that such variants or homologs provide at least some activity (for example, at least 50%, 60%, 75%, 80%, 85%, 90%, 95%, 100% or more) of the growth inhibition (GI) activity or mortality against a coleopteran pest as the GI activity of DIG-17. GI activity against Colorado potato beetle can be determined, for example, using methods described herein.

In another embodiment, the invention provides an isolated, treated, or formulated DIG-17 insecticidal toxin polypeptide comprising a DIG-17 core toxin segment selected from the group consisting of (d) a polypeptide comprising the amino acid sequence of residues 2 to 1158 of SEQ ID NO:2;
(e) polypeptide comprising an amino acid sequence having at least 90% sequence identity to the amino acid sequence of residues 2 to 1158 of SEQ ID NO:2; and
(f) polypeptide comprising an amino acid sequence of residues 2 to 1158 of SEQ ID NO:2, with up to 20 amino acid substitutions, deletions, or modifications that do not adversely affect expression or activity of the toxin of SEQ ID NO:2; or an insecticidal active fragment of (a), (b), or (c).

In certain embodiments, the DIG-17 insecticidal toxin polypeptide core toxin segment comprises (d') the amino acid sequence of residues from approximately 1 to 1158 of SEQ ID NO:2; (e') an amino acid sequence having at least 80%, 85%, 90%, 91%, 92%, 93%, 94%, 95%, 96%, 97%, 98%, or 99% sequence identity to the amino acid sequence of residues from approximately 1 to 1158 of SEQ ID NO:2; and (f') an amino acid sequence of residues from approximately 1 to 1158 of SEQ ID NO:2, with up to 20 amino acid substitutions, deletions, or modifications that retain the activity of the toxin of SEQ ID NO:2; or an insecticidal active fragment of either (d'), (e') or (f'). In further embodiments, the DIG-17 insecticidal toxin polypeptide of (d), (e), (f), (d'), (e') or (f') can be linked to a C-terminal protoxin, e.g., the C-terminal protoxin of cry1Ab or cry1Ac/cry1Ab chimeric toxin. In related embodiments, the invention provides a recombinant polynucleotide (e.g., a DNA construct) that comprises a nucleotide sequence encoding the DIG-17 insecticidal toxin polypeptide of (d), (e), (f), (d'), (e') or (f') which is operably linked to a heterologous promoter that is not derived from *Bacillus thuringiensis* and is capable of driving expression of the encoded DIG-17 insecticidal toxin polypeptide in a plant. Examples of heterologous promoters are described herein. The invention also provides a transgenic plant that comprises the DNA construct stably incorporated into its genome and a method for protecting a plant from a pest comprising introducing the construct into said plant.

In another embodiment, the invention provides an isolated polypeptide molecules have been removed from the native environment of DIG-17 and placed in a different environment by the hand of man. Thus, isolated polynucleotide and polypeptide molecules include DNA and protein molecules, respectively, that have been purified, concentrated, or otherwise rendered substantially free of *Bacillus thuringiensis* cellular material. Embodiments of a "purified" DIG-17 insecticidal polypeptide or encoding polynucleotide molecule can have less than about 30%, less than about 20%, less than about 10%, less than about 9%, less than about 8%, less than about 7%, less than about 6%, less than about 5%, less than about 4%, less than about 3%, less than about 2%, or less than about 1% (by dry weight) of contaminating proteins (e.g., from *Bacillus thuringiensis*). When the isolated DIG-17 insecticidal polypeptide or polynucleotide is produced recombinantly, then a "purified" DIG-17 insecticidal polypeptide or polynucleotide is one where less than about 30%, less than about 20%, less than about 10%, less than about 5%, less than about 4%, less than about 3% or less than about 2%, or less than about 1% (by dry weight) of contaminating materials from culture medium material, chemical precursors, and/or or non-DIG-17 insecticidal polypeptide or polynucleotide represent.

BRIEF DESCRIPTION OF THE SEQUENCES

SEQ ID NO:1 is a DNA sequence encoding a DIG-17 toxin; 3474 nt.

SEQ ID NO:2 is a deduced full-length DIG-17 protein sequence; 1158 aa.

SEQ ID NO:3 is a DNA sequence comprising DIG-17 core toxin segment; 1992 nt.

SEQ ID NO:4 is maize-optimized DNA sequence encoding DIG-17 core toxin segment, also known as DIG-90; 2001 nt.

SEQ ID NO:5 is the protein encoded by DIG-17 core toxin DNA sequence SEQ ID NO:4 and is known as DIG-90; 666 aa.

SEQ ID NO:6 is a maize-optimized DNA sequence encoding a chimeric protein comprising DIG-17 core toxin protein linked to Cry1Ab protoxin c-terminal segment; 3630 nt. This protein is known as DIG-79.

SEQ ID NO:7 is a chimeric DIG-17/Cry1Ab (DIG-79) polypeptide sequence encoded by SEQ ID NO:6; 1209 aa.

SEQ ID NO:8 is the protein encoded by maize-optimized DNA sequence of SEQ ID NO:4 (DIG-90); 666 aa

DETAILED DESCRIPTION OF THE INVENTION

DIG-17 Insecticidal Toxins

In addition to the full-length DIG-17 toxin of SEQ ID NO:2, the invention encompasses insecticidal active variants thereof. By the term "variant", applicants intend to include fragments, certain deletion and insertion mutants, and certain fusion or chimeric proteins that retain the activity of full-length DIG-17 toxin. As used herein, each reference to variants or homologs that "retain the activity" of DIG-17 toxin means that such variants or homologs provide at least some activity (e.g., at least 50%, 60%, 75%, 80%, 85%, 90%, 95%, 100% or more) of the growth inhibition (GI) activity or mortality against a coleopteran pest as the activity of DIG-17. For example, GI activity against Colorado potato beetle can be determined using the method described herein. Full-length DIG-17 includes three-domains generally associated with a Cry toxin. As a preface to describing variants of the DIG-17 toxin that are included in the invention, it will be useful to briefly review the architecture of three-domain Cry toxins in general and of the DIG-17 protein toxin in particular.

A majority of *Bacillus thuringiensis* delta-endotoxin crystal protein molecules are composed of two functional segments. The protease-resistant core toxin is the first segment and corresponds to about the first half of the protein molecule. The full ~130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., 1989). The protoxin segment may thus convey a partial insect specificity for the toxin by limiting the accessibility of the core to the insect by reducing the protease processing of the toxin molecule (Haider et al., 1986) or by reducing toxin solubility (Aronson et al., 1991). B.t. toxins, even within a certain class, vary to some extent in length and in the precise location of the transition from the core toxin segment to protoxin segment. The transition from core toxin segment to protoxin segment will typically occur at between about 50% to about 60% of the full-length toxin. SEQ ID NO:2 discloses the 1158 amino acid sequence of the partial DIG-17 polypeptide, of which the N-terminal 666 amino acids comprise a DIG-17 core toxin segment. The native DIG-17 core toxin segment is referred to herein as DIG-90. The 5'-terminal 1998 nucleotides of SEQ ID NO:1 provide a coding region for DIG-90. SEQ ID NO:6 discloses a fusion or chimeric protein containing the core sequence of DIG-17, also known as DIG-90, and a Cry1Ab tail. This fusion protein is referred to herein as DIG-79.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains with the features described below (reviewed in de Maagd et al., 2003).

Domain I is a bundle of seven alpha helices where helix five is surrounded by six amphipathic helices. This domain has been implicated in pore formation and shares homology with other pore forming proteins including hemolysins and colicins. Domain I of the DIG-17 protein comprises amino acid residues approximately 1-295 of SEQ ID NO:2.

Domain II is formed by three anti-parallel beta sheets packed together in a beta prism. The loops of this domain play important roles in binding insect midgut receptors. In Cry1A proteins, surface exposed loops at the apices of Domain II beta sheets are involved in binding to Lepidopteran cadherin receptors. Cry3Aa Domain II loops bind a membrane-associated metalloprotease of *Leptinotarsa decemlineata* Say (CPB) in a similar fashion (Ochoa-Campuzano et al., 2007). Domain II shares homology with certain carbohydrate-binding proteins including vitelline and jacaline. Domain II of the DIG-17 protein comprises amino acid residues approximately 295-522 of SEQ ID NO:2.

Domain III is a beta sandwich of two anti-parallel beta sheets. Structurally this domain is related to carbohydrate-binding domains of proteins such as glucanases, galactose oxidase, sialidase, and others. Conserved B.t. sequence blocks 2 and 3 map near the N-terminus and C-terminus of Domain II, respectively. Hence, these conserved sequence blocks 2 and 3 are approximate boundary regions between the three functional domains. These regions of conserved DNA and protein homology have been exploited for engineering recombinant B.t. toxins (U.S. Pat. No. 6,090,931, WO1991001087, WO1995006730, U.S. Pat. No. 5,736,131, U.S. Pat. No. 6,204,246, U.S. Pat. No. 6,780,408, WO1998022595, US Patent Application No. 20090143298, and U.S. Pat. No. 7,618,942). Domain III of the DIG-17 protein comprises amino acid residues approximately 522-666 of SEQ ID NO:2.

In lepidopteran insects it has been reported that Cry1A toxins bind certain classes of receptor proteins including cadherins, aminopeptidases and alkaline phosphatases, others remain to be identified (Honée et al., 1991; Pigott and Ellar, 2007). In coleopteran insects, two receptors have been identified for Cry3Aa; in Colorado potato beetle an ADAM metalloprotease (Biochemical and Biophysical Research Communications 362 (2007) 437-442), in Tenebrio a cadherin has been identified (THE JOURNAL OF BIOLOGICAL CHEMISTRY VOL. 284, NO. 27, pp. 18401-18410, Jul. 3, 2009). Given the diversity of *Bacillus thuringiensis* toxins and pests it is anticipated that additional receptors will be identified that will include additional classes of proteins and membrane surface substituents.

It has been reported that α-helix 1 of Domain I is removed following receptor binding. Aronson et al. (1999) demonstrated that Cry1Ac bound to brush border membrane vesicles (BBMV) was protected from proteinase K cleavage beginning at residue 59, just after α-helix 1; similar results were cited for Cry1Ab. Gomez et al. (2002) found that Cry1Ab oligomers formed upon BBMV receptor binding lacked the α-helix 1 portion of Domain I. Also, Soberon et al. (2007) have shown that N-terminal deletion mutants of Cry1Ab and Cry1Ac which lack approximately 60 amino acids encompassing α-helix 1 on the three dimensional Cry structure are capable of assembling monomers of molecular weight about 60 kDa into pre-pores in the absence of cadherin binding. These N-terminal deletion mutants were reported to be active on Cry-resistant insect larvae. Furthermore, Diaz-Mendoza et al. (2007) described Cry1Ab fragments of 43 kDa and 46 kDa that retained activity on Mediterranean corn borer (*Sesamia nonagrioides*). These fragments were demonstrated to include amino acid residues 116 to 423 of Cry1Ab; however the precise amino acid sequences were not elucidated and the mechanism of activity of these proteolytic fragments is unknown. The results of Gomez et al. (2002), Soberon et al. (2007) and Diaz-Mendoza et al. (2007) contrast with those of Hofte et al. (1986), who reported that deletion of 36 amino acids from the N-terminus of Cry1Ab resulted in loss of insecticidal activity.

Amino Terminal Deletion Variants of DIG-17

In one of its aspects, the invention provides DIG-17 variants in which all or part of one or more α-helices are deleted to improve insecticidal activity and avoid development of resistance by insects. These modifications are made to provide DIG-17 variants with improved attributes, such as improved target pest spectrum, potency, and insect resistance management. In some embodiments of the subject invention, the subject modifications may affect the efficiency of protoxin activation and pore formation, leading to insect intoxication. More specifically, to provide DIG-17 variants with improved attributes, step-wise deletions are described that remove part of the DNA sequence encoding the N-terminus. Such deletions remove all of α-helix 1 and all or part of α-helix 2 in Domain I, while maintaining the structural integrity of the α-helices 3 through 7. The subject invention therefore relates in part to improvements to Cry protein efficacy made by engineering the α-helical components of Domain I for more efficient pore formation. More specifically, the subject invention provides improved DIG-17 proteins designed to have N-terminal deletions in regions with putative secondary structure homology to α-helices 1 and 2 in Domain I of Cry1 proteins.

In designing coding sequences for the N-terminal deletion variants, an ATG start codon, encoding methionine, is inserted at the 5' end of the nucleotide sequence designed to express the deletion variant. For sequences designed for use in transgenic plants, it may be of benefit to adhere to the "N-end rule" of Varshaysky (1997). It is taught that some amino acids may contribute to protein instability and degradation in eukaryotic cells when displayed as the N-terminal residue of a protein. For example, data collected from observations in yeast and mammalian cells indicate that the N-terminal destabilizing amino acids are F, L, W, Y, R, K, H, I, N, Q, D, E and possibly P. While the specifics of protein degradation mechanisms may differ somewhat between organisms, the conservation of identity of N-terminal destabilizing amino acids seen above suggests that similar mechanisms may function in plant cells. For instance, Worley et al. (1998) found that in plants the N-end rule includes basic and aromatic residues. It may be that proteolytic cleavage by plant proteases near the start of α-helix 3 of subject B.t. insecticidal proteins expose a destabilizing N-terminal amino acid. Such processing may target the cleaved proteins for rapid decay and limit the accumulation of the B.t. insecticidal proteins to levels insufficient for effective insect control. Accordingly, for certain examples of N-terminal deletion variants that begin with one of the destabilizing amino acids, a codon that specifies a G (glycine) amino acid can be added between the translational initiation methionine and the destabilizing amino acid.

Chimeric Toxins

Chimeric proteins utilizing the core toxin domains of one Cry toxin fused to the protoxin segment of another Cry toxin have previously been reported. DIG-17 variants include toxins comprising an N-terminal toxin core segment of a DIG-17 insecticidal toxin (which may be full-length or have the N-terminal deletions described above) fused to a heterologous protoxin segment at some point past the end of the core toxin segment. The transition to the heterologous protoxin segment can occur at approximately the core toxin/protoxin junction or, in the alternative, a portion of the native protoxin (extending past the core toxin segment) can be retained with the transition to the heterologous protoxin occurring downstream. As an example, a chimeric toxin of the subject invention has the full core toxin segment of DIG-17 (approximately, amino acids 1 to 666) and a heterologous protoxin (amino acids 667 to the C-terminus). In one embodiment, the DIG-17 core toxin (DIG-90) is fused to a heterologous protoxin segment derived from a Cry1Ab delta-endotoxin, for example, as shown in SEQ ID NO:7, which discloses the amino acid sequence of DIG-79 (DIG-17 core toxin segment (DIG-90) and a Cry1Ab protoxin segment). SEQ ID NO:6 discloses a DNA sequence encoding the foregoing chimeric toxin DIG-79, which coding sequence has been designed for expression in maize cells.

In additional embodiments, the invention provides a chimeric protein that includes a protein fusion tag which is linked to the full core toxin segment of DIG-17 and a protoxin sequence (e.g., DIG-17 protoxin or a heterologous protoxin). The protein fusion tag can be linked at the N-terminus (e.g., at amino acid 1 or 2 of DIG-17 core toxin segment) or, alternatively, the protein fusion tag can be linked at the C-terminus of the protoxin sequence. The protein fusion tag can be a poly-histidine, poly-arginine, haloalkane dehalogenase, streptavidin-binding, glutathione s-transferase (GST), maltose-binding protein (MBP), thioredoxin, small ubiquitin-like modifier (SUMO), N-utilization substance A (NusA), protein disulfide isomerase I (DsbA), Mistic, Ketosteroid isomerase (KSI), or TrpE, c-myc, hemaglutinin antigen (HA), FLAG, 1D4, calmodulin-binding peptide, chitin-binding domain, cellulose-binding domain, S-tag, or Softag3 protein fusion tag. These can be used in methods of producing, isolating, or purifying any DIG-17 insecticidal toxin of the invention. The invention also provides a recombinant polynucleotide, e.g., a construct, encoding the fusion tag which is linked to the DIG-17 insecticidal toxin of the invention.

Protease Sensitivity Variants

Insect gut proteases typically function in aiding the insect in obtaining needed amino acids from dietary protein. The best understood insect digestive proteases are serine proteases, which appear to be the most common type (Englemann and Geraerts, 1980), particularly in lepidopteran species. Coleopteran insects have guts that are more neutral to acidic than are lepidopteran guts. The majority of coleopteran larvae and adults, for example CPB, have slightly acidic midguts, and cysteine proteases provide the major proteolytic activity (Wolfson and Murdock, 1990). More precisely, Thie and Houseman (1990) identified and characterized the cysteine proteases, cathepsin B-like and cathepsin H-like, and the aspartyl protease, cathepsin D-like, in CPB. Gillikin et al. (1992) characterized the proteolytic activity in the guts of western corn rootworm larvae and found primarily cysteine proteases. U.S. Pat. No. 7,230,167 disclosed that a protease activity attributed to cathepsin G exists in western corn rootworm. The diversity and different activity levels of the insect gut proteases may influence an insect's sensitivity to a particular B.t. toxin.

In another embodiment, of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to affect protein processing at desired deletion points within the midgut of susceptible larvae. Serine proteases that can be exploited in such fashion include lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation. Modified Cry proteins generated either by gene deletion or by introduction of protease cleavage sites have improved activity on lepidopteran pests such as *Ostrinia nubilalis, Diatraea grandiosella, Helicoverpa zea, Agrotis ipsilon, Spodoptera frugiperda, Spodoptera exigua, Diatraea saccharalis, Loxagrotis albicosta*, Coleopteran pests such as western corn rootworm, southern corn rootworm, northern corn rootworm (i.e. *Diabrotica* spp.), and other target pests.

Coleopteran serine proteases such as trypsin, chymotrypsin and cathepsin G-like protease, coleopteran cysteine proteases such as cathepsins (B-like, L-like, O-like, and K-like proteases) (Koiwa et al., 2000; and Bown et al., 2004), Coleopteran metalloproteases such as ADAM10 (Ochoa-Campuzano et al., 2007), and coleopteran aspartic acid proteases such as cathepsins D-like and E-like, pepsin, plasmepsin, and chymosin may further be exploited by engineering appropriate recognition sequences at desired processing sites to affect Cry protein processing within the midgut of susceptible larvae of certain insect pests.

A preferred location for the introduction of such protease cleavage sites is within the "spacer" region between α-helix2B and α-helix3. A second preferred location for the introduction of protease cleavage sites is within the spacer region between α-helix3 and α-helix4. Modified DIG-17 insecticidal toxin proteins are generated either by gene deletion or by introduction of protease cleavage sites to provide improved activity on insect pests including but not limited to Colorado potato beetle (CPB), alfalfa weevil, boll weevil, Japanese beetle, and the like.

Various technologies exist to enable determination of the sequence of the amino acids which comprise the N-terminal or C-terminal residues of polypeptides. For example, automated Edman degradation methodology can be used in sequential fashion to determine the N-terminal amino acid sequence of up to 30 amino acid residues with 98% accuracy per residue. Further, determination of the sequence of the amino acids comprising the carboxy end of polypeptides is also possible (Bailey et al., 1992; U.S. Pat. No. 6,046,053). Thus, in some embodiments, B.t. Cry proteins which have been activated by means of proteolytic processing, for example, by proteases prepared from the gut of an insect, may be characterized and the N-terminal or C-terminal amino acids of the activated toxin fragment identified. DIG-17 variants produced by introduction or elimination of protease processing sites at appropriate positions in the coding sequence to allow, or eliminate, proteolytic cleavage of a larger variant protein by insect, plant or microorganism proteases are within the scope of the invention. The end result of such manipulation is understood to be the generation of toxin fragment molecules having the same or better activity as the intact (full length) toxin protein.

Domains of the DIG-17 Toxin

The separate domains of the DIG-17 toxin, (and variants that are 90%, 91%, 92%, 93, 94%, 95%, 96%, 97%, 98%, or 99% identical to such domains) are expected to be useful in forming combinations with domains from other Cry toxins to provide new toxins with increased spectrum of pest toxicity, improved potency, or increased protein stability. Domain I of the DIG-17 protein comprises approximately amino acid residues 1 to 295 of SEQ ID NO:2. Domain II of the DIG-17 protein comprises approximately amino acid residues 295 to 522 of SEQ ID NO:2. Domain III of the DIG-17 protein comprises approximately amino acid residues 522 to 666 of SEQ ID NO:2. Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Domain II is involved in receptor binding, and Domain III binds certain classes of receptor proteins and perhaps participates in insertion of an oligomeric toxin pre-pore. Some Domain III substitutions in other toxins have been shown to produce superior toxicity against *Spodoptera exigua* (de Maagd et al., 1996) and guidance exists on the design of the Cry toxin domain swaps (Knight et al., 2004).

Methods for generating recombinant proteins and testing them for pesticidal activity are well known in the art (see, for example, Naimov et al., 2001; de Maagd et al., 1996; Ge et al., 1991; Schnepf et al., 1990; Rang et al., 1999). Domain I from Cry1A and Cry3A proteins has been studied for the ability to insert and form pores in membranes. α-helices 4 and 5 of Domain I play key roles in membrane insertion and pore formation (Walters et al., 1993; Gazit et al., 1998; Nunez-Valdez et al., 2001), with the other helices proposed to contact the membrane surface like the ribs of an umbrella (Bravo et al., 2007; Gazit et al., 1998).

DIG-17 Variants Created by Making a Limited Number of Amino Acid Deletions, Substitutions, or Additions Amino acid deletions, substitutions, and additions to the amino acid sequence of SEQ ID NO:2 can readily be made in a sequential manner and the effects of such variations on insecticidal activity can be tested by bioassay. Provided the number of changes is limited in number, such testing does not involve unreasonable experimentation. The invention includes insecticidal active variants of the core toxin (approximately amino acids 1 to 666 of SEQ ID NO:2), in which up to 2, up to 3, up to 4, up to 5, up to 10, up to 15, or up to 20 amino acid additions, deletions, or substitutions have been made.

The invention includes DIG-17 insecticide toxins having a core toxin segment that is 90%, 91%, 92%, 93, 94%, 95%, 96%, 97%, 98%, or 99% identical to amino acids 1 to 666 of SEQ ID NO:2. Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Class of Amino Acid | Examples of Amino Acids |
| --- | --- |
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity. Pesticidal activity can be determined in various ways including for example, by assessing mortality or growth inhibition (GI) activity against a coleopteran pest such as the Colorado potato beetle.

Variant proteins can also be designed that differ at the sequence level but that retain the same or similar overall essential three-dimensional structure, surface charge distribution, and the like. See, for example, U.S. Pat. No. 7,058,515; Larson et al. (2002); Stemmer (1994a, 1994b, 1995) and Crameri et al. (1996a, 1996b, 1997). U.S. Pat. No. 8,513,492 B2

Nucleic Acids and Nucleic Acid Constructs

Isolated nucleic acids (polynucleotides) encoding DIG-17 insecticidal toxins are one aspect of the present invention. This includes nucleic acids encoding any of the DIG-17 insecticidal toxins disclosed herein, including for example SEQ ID NO:2 and SEQ ID NO:6, and complements thereof, as well as other nucleic acids that encode insecticidal variants of SEQ ID NO:2. The term "isolated" is defined herein above. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Recombinant molecular biology methods can be used to combine the isolated polynucleotide encoding any of the DIG-17 insecticidal toxins (including variants) disclosed herein to a heterologous nucleic acid sequence, which can include a promoter, enhancer, multiple cloning site, expression construct, and/or a vector sequence to thereby make a nucleic acid construct of the invention.

Gene Synthesis

Genes encoding the DIG-17 insecticidal toxins described herein can be made by a variety of methods well-known in the art. For example, synthetic gene segments and synthetic genes can be made by phosphite tri-ester and phosphoramidite chemistry (Caruthers et al., 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding DIG-17 insecticidal toxins can be made for example, by synthetic construction by methods currently practiced by any of several commercial suppliers. (e.g., U.S. Pat. No. 7,482,119). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a DIG-17 insecticidal toxin, a coding sequence can be designed by reverse translating the coding sequence using synonymous codons preferred by the intended host, and then refining the sequence using alternative synonymous codons to remove sequences that might cause problems in transcription, translation, or mRNA stability. Further, synonymous codons may be employed to introduce stop codons in the non-DIG-17 reading frames (i.e. reading frames 2, 3, 4, 5 and 6) to eliminate spurious long open reading frames.

Quantifying Polypeptide or Nucleic Acid Sequence Identity

The percent identity of two amino acid sequences or of two nucleic acid sequences is determined by first aligning the sequences for optimal comparison purposes. The percent identity between the two sequences is a function of the number of identical positions shared by the sequences (i.e. percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST (Altschul et al., 1997) can be utilized to obtain gapped alignments for comparison purposes. Alternatively, PSI-Blast can be used to perform an iterated search that detects distant relationships between molecules (Altschul et al., 1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available from the European Molecular Biology Open Software Suite (EMBOSS) web site). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (available from the European Molecular Biology Open Software Suite (EMBOSS) web site). GAP Version 10 may be used to determine sequence identity or similarity using the following parameters: for a nucleotide sequence, % identity and % similarity are found using GAP Weight of 50 and Length Weight of 3, and the nwsgapdna.cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts.

The toxin-encoding genes of the subject invention can be introduced into a wide variety of microbial or plant hosts. Expression of the toxin gene results, directly or indirectly, in the intracellular production and maintenance of the pesticidal protein. With suitable microbial hosts, e.g., *Pseudomonas*, the microbes can be applied to the environment of the pest, where they will proliferate and be ingested. The result is a control of the pest. Alternatively, the microbe hosting the toxin gene can be treated under conditions that prolong the activity of the toxin and stabilize the recombinant host cell. The treated cell, which comprises a treated toxin polypeptide of the invention that retains insecticidal activity, can be applied to the environment of the target pest to control the pest.

Where the B.t. toxin gene is introduced via a suitable DNA construct, e.g., a vector, into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms such as bacteria, e.g., genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*. Of further interest are fungi, particularly yeast, e.g., genera *Saccharomyces, Cryptococcus, Kluyveromyces, Sporobolomyces, Rhodotorula*, and *Aureobasidium*, and of particular interest are phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Isolated Toxin Polypeptides and Compositions of the Invention.

The DIG-17 insecticidal toxin polypeptides of the invention can be treated or prepared, for example, to make a formulated pesticide composition. Examples of formulated pesticide compositions include protein composition, sprayable protein composition, a bait matrix, or any other appropriate delivery system. In one example, B.t. cells or recombinant host cells expressing a DIG-17 insecticidal toxin of the invention can be cultured using standard media and fermentation techniques. Upon completion of the fermentation cycle, the B.t. spores or other recombinant host cells and/or toxin crystals from the fermentation broth can be isolated by methods known in the art. B.t. spores or recombinant host cells also can be treated prior to being applied or formulated for application to plants. For example, isolated B.t. spores and/or toxin crystals can be chemically treated to prolong insecticidal activity to thereby create a treated polypeptide of the invention. Methods of growing B.t. toxin polypeptides in recombinant hosts and then treating the B.t. to prolong pesticidal activity are known and have been published. See, e.g., U.S. Pat. Nos. 4,695,462, and 4,695,455 and Gaertner et al., 1993.

The isolated or treated DIG-17 insecticidal toxin of the invention can be formulated into compositions of finely-divided particulate solids granules, pellets, wettable powders, dusts, aqueous suspensions or dispersions, emulsions, spray, liquid concentrate, or other insecticide formulations. These insecticide formulations are made by combining a DIG-17 insecticide polypeptide herein with one or more inert ingredients such as, for example, minerals (phyllosilicates, carbonates, sulfates, phosphates, and the like), botanical materials (powdered corncobs, rice hulls, walnut shells, and the like), adjuvants, diluents, surfactants, dispersants, other inert carriers and combinations thereof to facilitate handling and application to control one or more target pests. Such formulation ingredients are known in the art, as are methods of application and methods of determining levels of the B.t. spores and/or isolated DIG-17 polypeptide crystals that provide desired insecticidal activity.

Methods for Controlling Insect Pests.

When an insect comes into contact with an effective amount of DIG-17 toxin disclosed herein, which is delivered via an insecticide composition (e.g., a formulated protein composition (s), sprayable protein composition(s), a bait matrix), transgenic plant expression, or another delivery system, the results are typically death of the insect, or the insects do not feed upon the source which makes the toxins available to the insects.

The subject protein toxins can be "applied" or provided to contact the target insects in a variety of ways. For example, the DIG-17 insecticidal toxin of the invention can be applied after being formulated with adjuvants, diluents, carriers, etc. to provide compositions in the form of finely-divided particulate solids, granules, pellets, wettable powders, dusts, aqueous suspensions or dispersions, and emulsions. Alternatively, the DIG-17 insecticidal polypeptide can be delivered by transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants.

The DIG-17 insecticidal toxin disclosed herein can be used to protect practically any type of plant from damage by an insect pest. Examples of such plants include potato, eggplant, tomato, pepper, tobacco, and other plants in the nightshade family. Other examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the DIG-17 insecticidal toxin insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. Nos. 5,177,010, 8,710,207, European Patent No. EP131624B1, European Patent No. EP159418B1, European Patent No. EP176112B1, U.S. Pat. No. 5,149,645, EP120516B1, U.S. Pat. No. 5,464,763, U.S. Pat. No. 4,693,976, European Patent No. EP116718B1, European Patent No. EP290799B1, European Patent No. EP320500B1, European Patent No. EP604662B1, U.S. Pat. No. 7,060,876, U.S. Pat. No. 6,037,526, U.S. Pat. No. 6,376,234, European Patent No. EP292435B1, U.S. Pat. No. 5,231,019, U.S. Pat. No. 5,463,174, U.S. Pat. No. 4,762,785, U.S. Pat. No. 5,608,142, and U.S. Pat. No. 5,159,135. Other transformation technology includes WHISKERS™ technology, see U.S. Pat. No. 5,302,523 and U.S. Pat. No. 5,464,765. Electroporation technology has also been used to transform plants, see WO1987006614, U.S. Pat. No. 5,472,869, U.S. Pat. No. 5,384,253, WO199209696, U.S. Pat. No. 6,074,877, WO1993021335, and U.S. Pat. No. 5,679,558. In addition to numerous technologies for transforming plants, the type of tissue which is contacted with the foreign genes may vary as well. Such tissue would include but would not be limited to embryogenic tissue, callus tissue type I and type II, hypocotyl, meristem, and the like. Almost all plant tissues may be transformed during dedifferentiation using appropriate techniques within the skill of an artisan.

Genes encoding DIG-17 insecticidal toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent No. EP120516B1; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as phosphinothricin Bialaphos, Kanamycin, Neomycin, G418, Bleomycin, Hygromycin, or a gene which codes for resistance or tolerance to glyphosate, methotrexate, imidazolinones, sulfonylureas and triazolopyrimidine herbicides, such as chlorosulfuron, bromoxynil, dalapon and the like. Of further interest are genes conferring tolerance to herbicides such as haloxyfop, quizalofop, diclofop, and the like, as exemplified by AAD genes (US Patent Application No. 20090093366). The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831. For example, the DIG-17 insecticidal toxin of the invention can be optimized for expression in a dicot such as potato, eggplant, tomato, pepper, tobacco, and another plant in the nightshade family. The DIG-17 insecticidal toxin of the invention can also be optimized for expression in other dicots, or in monocots such as *Zea mays* (corn). Also, advantageously, plants encoding a truncated toxin will be used. The truncated toxin typically will encode about 55% to about 80% of the full-length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g., heat shock genes); light (e.g., RUBP carboxylase); hormone (e.g., glucocorticoid); antibiotic (e.g., tetracycline); metabolites; and stress (e.g., drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as Bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO2007053482), or phenoxy acids herbicides and aryloxyphenoxypropionates herbicides (see US Patent Application No. 20090093366). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g., other insect resistance conferred by B.t.-derived or other insecticidal proteins, insect resistance conferred by mechanisms such as RNAi and the like, nematode resistance, disease resistance, stress tolerance, improved nitrogen utilization, and the like), or output traits (e.g., high oils content, healthy oil composition, nutritional improvement, and the like). Such combinations may be obtained either through conventional breeding (breeding stack) or jointly as a novel transformation event involving the simultaneous introduction of multiple genes (molecular stack or co-transformation). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

Target Pests.

The DIG-17 insecticidal toxins of the invention are particularly suitable for use in control of insects pests. Coleopterans are one important group of agricultural, horticultural, and household pests which cause a very large amount of damage each year. This large insect order encompasses foliar- and root-feeding larvae and adults, including members of, for example, the insect families—Chrysomelidae, Coccinellidae, Curculionidae, Dermestidae, Elateridae, Scarabaeidae, Scolytidae, and Tenebrionidae. Included within these families are leaf beetles and leaf miners in the family Chrysomelidae, potato beetles (e.g., Colorado potato beetle (*Leptinotarsa decemlineata* Say), grape colaspis (*Colaspis brunnea* Fabricius), cereal leaf beetle (*Oulema melanopus* Linnaeus), sunflower beetle (*Zygogramma exclamationis* Fabricius), and beetles in the family Coccinellidae (e.g., Mexican bean beetle (*Epilachna varivestis* Mulsant)). Further examples are chafers and other beetles in the family Scarabaeidae (e.g., Japanese beetle (*Popillia japonica* Newman), northern masked chafer (white grub, *Cyclocephala borealis* Arrow), southern masked chafer (white grub, *Cyclocephala immaculata* Olivier), European chafer (*Rhizotrogus majalis* Razoumowsky), white grub (*Phyllophaga crinita* Burmeister), carrot beetle (*Ligyrus gibbosus* De Geer), and chafers of the genera *Holotrichia* spp and *Melolontha* spp.). Further examples of coleopteran insects are weevils (e.g., boll weevil (*Anthonomus grandis* Boheman), rice water weevil (*Lissorhoptrus oryzophilus* Kuschel), granary weevil (*Sitophilus grananus* Linnaeus), rice weevil (*Sitophilus oryzae* Linnaeus), and clover leaf weevil (*Hypera punctata* Fabricius)). Also included are maize billbug (*Sphenophorus maidis* Chittenden), flea beetles (e.g., corn flea beetle (*Chaetocnema pulicara* Melsheimer), and crucifer flea beetle (*Phyllotreta cruciferae* Goeze)), spotted cucumber beetle (*Diabrotica undecimpunctata*), and rootworms, (e.g., western corn rootworm (*Diabrotica virgifera virgifera* LeConte), northern corn rootworm (*Diabrotica barben* Smith & Lawrence), and southern corn rootworm (*Diabrotica undecimpunctata* howardi Barber)). Further examples of coleopteran pests are beetles of the family Rutelinae (shining leaf chafers) such as the genus *Anomala* (including *A. marginata, A. lucicola, A. oblivia* and *A. orientalis*). Additional coleopteran insects are carpet beetles from the family Dermestidae, wireworms from the family Elateridae (e.g., *Melanotus* spp., *Conoderus* spp., *Limonius* spp., *Agriotes* spp., *Ctenicera* spp., *Aeolus* spp.)), bark beetles from the family Scolytidae, and beetles from the family Tenebrionidae (e.g., *Eleodes* spp). Any genus listed above (and others), generally, can also be targeted as a part of the subject invention by insectidal compositions including DIG-17 insecticidal polypeptide alone or in combination with another insecticidal agent. Any additional insects in any of these genera (as targets) are also included within the scope of this invention.

Use of DIG-17 insecticidal toxins to control coleopteran pests of crop plants is contemplated. In some embodiments, Cry proteins may be economically deployed for control of insect pests that include but are not limited to, for example, rootworms such as western corn rootworm (*Diabrotica virgifera virgifera* LeConte), northern corn rootworm (*Diabrotica barberi* Smith & Lawrence), and southern corn rootworm (*Diabrotica undecimpunctata* howardi Barber), and grubs such as the larvae of *Cyclocephala borealis* (northern masked chafer), *Cyclocephala immaculate* (southern masked chafer), and *Popillia japonica* (Japanese beetle).

Lepidopterans are another important group of agricultural, horticultural, and household pests which cause a very large amount of damage each year. The invention provides use of DIG-17 toxins in combination with other insecticides to control insect pests within this order by is within the scope of this invention. This insect order encompasses foliar- and root-feeding larvae and adults, including members of, for example, the insect families Arctiidae, Gelechiidae, Geometridae, Lasiocampidae, Lymantriidae, Noctuidae, Pyralidae, Sesiidae, Sphingidae, Tineidae, and Tortricidae. Lepidopteran insect pests include, but are not limited to: *Achoroia grisella, Acleris gloverana, Acleris variana, Adoxophyes orana, Agrotis ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens* (tobacco budworm), *Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis* (European corn borer), *Paleacrita vernata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia ni,* (cabbage looper), *Udea rubigalis, Xylomyges curiails,* and *Yponomeuta padella.*

Use of the DIG-17 insecticidal toxins to control parasitic nematodes including, but not limited to, root knot nematode (*Meloidogyne incognita*) and soybean cyst nematode (*Heterodera glycines*) is also contemplated.

Antibody Detection of DIG-17 Insecticidal Toxins
Anti-Toxin Antibodies

Antibodies to the toxins disclosed herein, or to equivalent toxins, or fragments of these toxins, can readily be prepared using standard procedures in this art. Such antibodies are useful to detect the presence of the DIG-17 toxins.

Once the B.t. insecticidal toxin has been isolated, antibodies specific for the toxin may be raised by conventional methods that are well known in the art. Repeated injections into a host of choice over a period of weeks or months will elicit an immune response and result in significant anti-B.t. toxin serum titers. Preferred hosts are mammalian species and more highly preferred species are rabbits, goats, sheep and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin or keyhole limpet hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal toxin. Methods for producing MAbs have been practiced for over 20 years and are well known to those of ordinary skill in the art. Repeated intraperitoneal or subcutaneous injections of purified B.t. insecticidal toxin in adjuvant will elicit an immune response in most animals. Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1® Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff (1983), may be used; however, the HAT (hypoxanthine, aminopterin, thymidine) selection system, described by Littlefield (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

Detection Using Probes.

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization.

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(° C.)=81.5° C.+16.6(\log M)+0.41(\% GC)-0.61(\% \text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983).

$$T_m(° C.)=81.5° C.+16.6(\log [Na+])+0.41(\% GC)-0.61(\% \text{formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995). Also see Sambrook et al. (1989).

Hybridization of immobilized DNA on Southern blots with radioactively labeled gene-specific probes may be performed by standard methods (Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g., Sambrook et al., supra.) In general, hybridization and subsequent washes may be carried out under stringent conditions that allow for detection of target sequences with homology to the claimed toxin encoding genes. For double-stranded DNA gene probes, hybridization may be carried out overnight at 20° C. to 25° C. below the $T_m$ of the DNA hybrid in 6×SSPE, 5×Denhardt's Solution, 0.1% SDS, 0.1 mg/mL denatured DNA (20×SSPE is 3M NaCl, 0.2 M NaHPO$_4$, and 0.02M EDTA (ethylenediamine tetra-acetic acid sodium salt); 100× Denhardt's Solution is 20 gm/L Polyvinylpyrollidone, 20 gm/L Ficoll type 400 and 20 gm/L Bovine Serum Albumin (fraction V)).

Washes may typically be carried out as follows:
  Twice at room temperature for 15 minutes in 1×SSPE, 0.1% SDS (low stringency wash).
  Once at $T_m$−20° C. for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(° C.)=2(\text{number of } T/A \text{ base pairs})+4(\text{number of } G/C \text{ base pairs})$$

Washes may typically be carried out as follows:
  Twice at room temperature for 15 minutes 1×SSPE, 0.1% SDS (low stringency wash).
  Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

All patents, patent applications, provisional applications, and publications referred to or cited herein are incorporated by reference in their entirety to the extent they are not inconsistent with the explicit teachings of this specification.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

Unless specifically indicated or implied, the terms "a", "an", and "the" signify "at least one" as used herein.

All percentages are by weight and all solvent mixture proportions are by volume unless otherwise noted. All temperatures are in degrees Celsius.

Example 1

Isolation of a Gene Encoding DIG-17 Toxin

Nucleic acid encoding the insecticidal Cry protein designated herein as DIG-17 was isolated from B.t. strain PS217U4. Degenerate Forward and Reverse primers for Polymerase Chain Reactions (PCR) were designed and used to amplify a DNA fragment with homology to cry8-type genes from genomic DNA library. The amplified fragment was subcloned into a DNA vector for sequencing. The determined sequence of the amplified fragment was used for genome walking to obtain the complete open reading frame of DIG-17. SEQ ID NO:1 is the 3474 bp nucleotide sequence encoding the full-length DIG-17 protein. SEQ ID NO:2 is the 1158 amino acid sequence of the full-length DIG-17 protein deduced from SEQ ID NO:1.

The foregoing provides the sequences for an isolated polynucleotide according to the invention, which encodes and is suitable for producing an isolated, treated, or formulated DIG-17 insecticidal toxin polypeptide according to the invention.

Example 2

Design of a Plant-Optimized Version of the Coding Sequence for the DIG-17 B.t. Insecticidal Toxin One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. No. 6,166,302, and U.S. Pat. No. 5,380,831.

A DNA sequence having a maize codon bias was designed and synthesized to produce a DIG-17 chimeric insecticidal protein in transgenic monocot plants. A codon usage table for maize (Zea mays L.) was calculated from hundreds of protein coding sequences obtained from sequences deposited in GenBank. A resealed maize codon set was calculated after omitting any synonymous codon used less than about 10% of total codon uses for that amino acid.

Experimentally determined (native) DIG-17 DNA coding sequence (SEQ ID NO:3) was altered by codon substitutions to make a maize-codon-optimized DNA sequence (SEQ ID NO:4) encoding the DIG-17 protein core toxin of DIG-90 (SEQ ID NO:5). The resulting DNA sequence had the overall codon composition of the maize-optimized codon bias table. In similar fashion, codon substitutions to the native cry1Ab DNA sequence encoding the Cry1Ab protoxin segment were made such that the resulting DNA sequence (SEQ ID NO:6) had the overall codon composition of the maize-optimized codon bias table. Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased Resealed codon composition. A maize-optimized DNA sequence encoding DIG-17 core toxin, also referred to as DIG-90, is disclosed as SEQ ID NO:4.

Maize-optimized DNA coding sequence for DIG-17 core toxin (DIG-90) was fused to coding sequence for Cry1Ab protoxin segment of SEQ ID NO:6, thereby encoding chimeric protein DIG-17 core toxin-Cry1Ab protoxin (SEQ ID NO:7) which is referred to herein as DIG-79.

The foregoing provides several embodiments of the isolated polynucleotide according to the invention, including polynucleotides that are codon-optimized for expression of DIG-17 insecticidal core toxin (DIG-90) polypeptide of the invention. The foregoing also provides an isolated polynucleotide encoding a chimeric DIG-17 insecticidal toxin polypeptide according to the invention.

Example 3

Construction of Expression Plasmid Encoding DIG-90 (DIG-17 Core Toxin) and DIG-79 (Chimeric DIG-17 Toxin) in Bacterial Hosts Standard cloning methods were used in the construction of *Pseudomonas fluorescens* (Pf) expression plasmids engineered to produce DIG-90 (DIG-17 core toxin) and DIG-79 (chimeric DIG-17 toxin) encoded by the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAQUICK Gel Extraction kit (Qiagen) after agarose Tris-acetate gel electrophoresis. The linearized vector was treated with ANTARCTIC Phosphatase (NEB) to enhance formation of recombinant molecules.

A DNA fragment having the DIG-90 or DIG-79 coding sequence (CDS), as provided by SEQ ID NO:4 or 6, was subcloned into pDOW1169 at SpeI and SalI restriction sites, whereby the DIG-90 or DIG-79 CDS was placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). The expression plasmids (pDAB102022 for DIG-90; pDAB102021 for DIG-79) were transformed by electroporation into DC454 (a near wild-type *P. fluorescens* strain having mutations ΔpyrF and lsc::lacIQI), or derivatives thereof, recovered in SOC-Soy hydrolysate medium, and plated on selective medium (M9 glucose agar lacking uracil, Sambrook et al., supra). The transformation and selection methods are generally described in Squires et al. (2004), US Patent Application No. 20060008877, U.S. Pat. No. 7,681,799, and US Patent Application No. 20080058262, incorporated herein by reference. Recombinant colonies were identified by restriction digestion of miniprep plasmid DNA.

Production of DIG-90 and DIG-79 for characterization and insect bioassay was accomplished by shake-flask-grown *P. fluorescens* strains harboring expression constructs strains DPf13593 and DPf13698, respectively. Seed cultures grown in M9 medium supplemented with glucose and trace elements were used to inoculate defined minimal medium. Expression of the DIG-90 and DIG-79 coding sequences were induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al 2007 and US Patent Application No. 20060008877. in cells from *P. fluorescens* fermentations that produced insoluble B.t. insecticidal protein inclusion bodies (IB). Briefly, cells are lysed, IB pellet is collected by centrifugation, IB is resuspended and repeatedly washed by resuspension in lysis buffer until the supernatant becomes colorless and the IB pellet becomes firm and off-white in color. The final pellet is washed, resuspended in sterile-filtered distilled water containing 2 mM EDTA, and stored at −80° C.

IB preparations were analyzed by SDS_PAGE. Quantification of target bands was done by comparing densitometric values for the bands against Bovine Serum Albumin (BSA) samples run on the same gel to generate a standard curve. Target protein was subsequently extracted from the inclusion body using sodium carbonate buffer and gently rocking on a platform at 4° C. overnight. Solubilized DIG-90 and DIG-79 were centrifuged and the resulting supernatant is concentrated. The sample buffer was then changed to 10 mM CAPS (3-(cyclohexamino)1-propanesulfonic acid) pH10, using disposable PD-10 columns (GE Healthcare, Piscataway, N.J.).

The concentrated extract was analyzed and quantified by SDS_PAGE relative to background-subtracted BSA standards to generate a standard curve to calculate the concentration of DIG-90 or DIG-79.

The foregoing provides isolated polynucleotides, including nucleic acid constructs, and isolated DIG-17 insecticidal polypeptides according to the invention.

Example 4

Insect Activity of DIG-90 Insecticidal Toxin

DIG-90 was tested and found to have insecticidal activity on larvae of the coleopteran insect, the Colorado potato beetle (*Leptinotarsa decemlineata*). In diet based insect bioassays DIG-90 did not show activity against western corn rootworm (*Diabrotica virgifera virgifera* LeConte).

Bioassays were conducted in 128-well plastic trays. Each well contained one 1.5 cm diameter Eggplant (*Solanum melongena*) "Black Beauty" leaf disk cut with a cork borer. Test leaf disks were treated with 9 μg/mL DIG-90. Leaf disks used as positive controls for insecticide activity were treated with 1 μg/mL of Cry3Aa toxin. Negative control leaf disks were treated with water or were left untreated.

Treated leaf disks were allowed to dry and then one Colorado potato beetle was added to each well. Sixteen replications were completed for each treatment listed above. After three days incubation, the estimated percentage of leaf disk damage, the number of dead insects, and the weight of surviving insects were recorded. Bioassay trays were held under controlled environmental conditions (28° C., ~40% Relative Humidity, 16:8 (Light:Dark)). Percent mortality and percent growth inhibition were calculated for each treatment. Growth inhibition (GI) is calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Bioassay results are summarized in Table 2 and Table 3, below. DIG-90 was tested and found to have insecticidal activity on larvae of the coleopteran insect, Colorado potato beetle (*Leptinotarsa decemlineata*). DIG-90 also showed a surprising 65% growth inhibition, below.

TABLE 2

| Leaf Treatment | Insecticide Dose (ug/cm$^2$) | Number of Insects Tested | Estimated Leaf Damage (%) | Percent Mortality | GI (%) |
|---|---|---|---|---|---|
| DIG-90 | 9 | 16 | 45 | 62.5 | 65 |
| Cry7Ab (Positive Control) | 9 | 16 | 10 | 81 | 99.5 |
| Cry1Ac1Ab (Negative Control) | 9 | 16 | 90 | 6.3 | −63.3 |
| CAPS Buffer (Negative Control) | 0 | 16 | 75 | 18.8 | 0 |
| UNTREATED | 0 | 16 | 95 | 0 | 0 |

TABLE 3

| Leaf Treatment | Insecticidal Dose (ug/cm$^2$) | Number of Insects Tested | Estimated Leaf Damage (%) | Percent Mortality |
|---|---|---|---|---|
| DIG-90 | 9 | 8 | 30 | 50 |
| Cry1Ac1Ab (Negative Control) | 9 | 8 | 20 | 38 |
| Cry3Aa (Positive Control) | 1 | 8 | 5 | 100 |
| CAPS BUFFER (Negative Control) | 0 | 8 | 50 | 0 |
| UNTREATED | 0 | 8 | 50 | 25 |

In diet based insect bioassays DIG-90 and DIG-79 insecticidal toxins did not demonstrate activity against western corn rootworm (WCR) when tested, indicating that DIG-90 and DIG-79 insecticidal toxins, when used as the only insecticide, is better suited to control Colorado potato beetle and similar susceptible coleoptera.

The foregoing describes a method of applying an isolated DIG-17 insecticidal polypeptide and controlling a coleopteran pest population in accordance with the invention.

Example 5

Agrobacterium Transformation

Standard cloning methods are used in the construction of binary plant transformation and expression plasmid. Restriction endonucleases and T4 DNA Ligase are obtained from NEB. Plasmid preparations are performed using the NucleoSpin® Plasmid Preparation kit or the NucleoBond® AX Xtra Midi kit (both from Macherey-Nagel), following the instructions of the manufacturers. DNA fragments are purified using the QIAquick PCR Purification Kit or the QIAEX II Gel Extraction Kit (both from Qiagen) after gel isolation.

DNA comprising a nucleotide sequence that encodes a DIG-17 insecticidal toxin, or fragments thereof such as DIG-90, or fusions such as DIG-79, is synthesized by a commercial vendor (e.g., DNA2.0, Menlo Park, Calif.) and supplied as cloned fragments in plasmid vectors. Other DNA sequences encoding other DIG-17 toxins are obtained by standard molecular biology manipulation of constructs containing appropriate nucleotide sequences. The DNA fragments encoding the modified DIG-17 fragments are joined to other DIG-17 insecticidal toxin coding region fragments or other B.t. (Cry) coding region fragments at appropriate restriction sites to obtain a coding region encoding the desired full-length DIG-17 toxin protein.

Full-length or modified coding sequences (CDS) for DIG-17 insecticidal toxin is subcloned into a plant expression plasmid at NcoI and SacI restriction sites. The resulting plant expression cassettes containing the appropriate Cry coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full-length and modified gene plant expression cassettes into a binary plant transformation plasmid if the Gateway® technology is utilized. The binary plant transformation vector includes a bacterial selectable marker gene that confers resistance to the antibiotic spectinomycin when the plasmid is present in *E. coli* and *Agrobacterium* cells. The binary vector plasmid also includes a plant-expressible selectable marker gene that is functional in the desired host plants, namely, the aminoglycoside phosphotransferase gene of transposon Tn5 (aphII) which encodes resistance to the antibiotics kanamycin, neomycin and G418.

Electro-competent cells of *Agrobacterium tumefaciens* strain Z707S (a streptomycin-resistant derivative of Z707; Hepburn et al., 1985) are prepared and transformed using electroporation (Weigel and Glazebrook, 2002). After electroporation, 1 mL of YEP broth (gm/L: yeast extract, 10; peptone, 10; NaCl, 5) are added to the cuvette and the cell-YEP suspension is transferred to a 15 mL culture tube for incubation at 28° C. in a water bath with constant agitation for 4 hours. The cells are plated on YEP plus agar (25 gm/L) with spectinomycin (200 µg/mL) and streptomycin (250 µg/mL) and the plates are incubated for 2-4 days at 28° C. Well separated single colonies are selected and streaked onto fresh YEP+agar plates with spectinomycin and streptomycin, and incubated at 28° C. for 1-3 days.

The presence of the DIG-17 insecticidal toxin gene insert in the binary plant transformation vector is performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before is extracted using Qiagen Spin Mini Preps, performed per manufacturer's instructions. Plasmid DNA from the binary vector used in the *Agrobacterium* electroporation transformation is included as a control. The PCR reaction is completed using Taq DNA polymerase from Invitrogen per manufacturer's instructions at 0.5× concentrations. PCR reactions are carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction is maintained at 4° C. after cycling. The amplification products are analyzed by agarose gel electrophoresis (e.g., 0.7% to 1% agarose, w/v) and visualized by ethidium bromide staining. A colony is selected whose PCR product is identical to the plasmid control.

Another binary plant transformation vector containing the DIG-17 insecticidal toxin gene insert is performed by restriction digest fingerprint mapping of plasmid DNA prepared from candidate *Agrobacterium* isolates by standard molecular biology methods well known to those skilled in the art of *Agrobacterium* manipulation.

The foregoing discloses nucleic acid constructs comprising a polynucleotide that encodes a DIG-17 insecticidal toxin polypeptide in accordance with the invention.

Example 6

Production of DIG-17 Insecticidal Toxins in Dicot Plants

*Arabidopsis* Transformation

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold Bio-Technology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 µmol/m$^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g., herbicide tolerance genes) are used.

Insect Bioassays of Transgenic *Arabidopsis*

Transgenic *Arabidopsis* lines expressing DIG-17 insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

The foregoing provides methods for making and using transgenic plants comprising DIG-17 insecticidal toxin polypeptides according to the invention.

Example 7

Generation of DIG-17 Superbinary Vectors for *Agrobacterium* Transformation

The *Agrobacterium* superbinary system is conveniently used for transformation of monocot plant hosts. DIG-17 coding sequence is cloned into the multiple cloning site of a binary vector using established methods for constructing and validating superbinary vectors. See, for example, European Patent No. EP604662B1 and U.S. Pat. No. 7,060,876. Standard molecular biological and microbiological methods are used to generate, verify, and validate superbinary plasmids. The foregoing provides an example of a nucleic acid construct comprising a polynucleotide encoding DIG-17 insecticidal toxin, according to the invention.

Example 8

Production of DIG-17 Insecticidal Toxins in Monocot Plants

*Agrobacterium*-Mediated Transformation of Maize

Seeds from a High II $F_1$ cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution is vortexed until a uniform suspension is achieved, and the concentration is adjusted to a final density of 200 Klett units, using a Klett-Summerson colorimeter with a purple filter, or an equivalent optical density measured at 600 nm ($OD_{600}$) Immature embryos are isolated directly into a micro centrifuge tube containing 2 mL of the infection medium. The medium is removed and replaced with 1 mL of the *Agrobacterium* solution with a density of 200 Klett units or equivalent $OD_{600}$, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 μM acetosyringone, 3.0 gm/L Gellan gum (PhytoTechnology Laboratories, Lenexa, Kans.), pH 5.8) for 5 days at 25° C. under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates are obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g., herbicide tolerance genes) are used.

Regeneration and Seed Production

For regeneration, the cultures are transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they are transferred to glass culture tubes containing SHGA medium (Schenk and Hildebrandt (1972) salts and vitamins); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

The foregoing provides methods for making and regenerating transgenic plants comprising DIG-17 insecticidal toxin polypeptides according to the invention.

Example 9

Bioassay of Transgenic Maize

Bioactivity of the DIG-17 insecticidal toxins produced in plant cells is demonstrated by conventional bioassay methods (see, for example Huang et al., 2006). In one assay of efficacy, various plant tissues or tissue pieces derived from a plant producing a DIG-17 insecticidal toxin are fed to target insects in a controlled feeding environment. In another bioactivity assay, protein extracts are prepared from various plant tissues derived from the plant producing the DIG-17 insecticidal toxin and the extracted proteins are incorporated into artificial diet bioassays. The results of each feeding assay are compared to similarly conducted bioassays that employ appropriate control tissues from host plants that do not produce a DIG-17 insecticidal toxin, or to other control samples. The results demonstrate that growth of target pests is significantly reduced by the plant producing the DIG-17 insecticidal toxin, as compared to the control.

Example 10

Production of DIG-17 Bt Insecticidal Proteins and Variants in Dicot Plants

*Arabidopsis* Transformation

*Arabidopsis thaliana* Col-01 is transformed using the floral dip method (Weigel and Glazebrook, 2002) with *Agrobacterium* containing a DIG-17 nucleic acid construct. The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 µM benzylaminopurine (10 µL/L of 1 mg/mL stock in DMSO) and 300 µL/L Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16:8 light:dark photoperiod. Approximately 4 weeks after dipping, the seeds are harvested.

*Arabidopsis* Growth and Selection

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron (Models CMP4030 or CMP3244; Controlled Environments Limited, Winnipeg, Manitoba, Canada) under long day conditions (16:8 light: dark photoperiod) at a light intensity of 120-150 µmol/m² sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and are transplanted into pots prepared with Sunshine Mix LP5. Transplanted plants are covered with a humidity dome for 3-4 days and placed in a Conviron under the above-mentioned growth conditions.

The foregoing provides methods for making and selecting transgenic dicot plants comprising DIG-17 insecticidal toxin polypeptides according to the invention.

Example 11

Transgenic *Glycine max* Comprising DIG-17

Ten to 20 transgenic $T_0$ *Glycine max* plants harboring expression vectors for nucleic acids comprising DIG-17 are generated by *Agrobacterium*-mediated transformation. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of split-seed soybeans. The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing binary plasmid comprising DIG-17. The *Agrobacterium tumefaciens* solution is diluted to a final concentration of λ=0.6 $OD_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/$m^2$ sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2EDTA$, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 mol/$m^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. There are no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of DIG proteins when cultured in vitro and in soil in the glasshouse.

The foregoing provides methods for making and selecting transgenic dicot plants (soybeans) comprising DIG-17 insecticidal toxin polypeptides according to the invention.

REFERENCES

An, G., Watson, B. D., Stachel, S., Gordon, M. P., Nester, E. W. (1985) New cloning vehicles for transformation of higher plants. EMBO J. 4:277-284.

Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schäffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillus thuringiensis* for lepidopteran larvae: factors involved in vivo and in the structure of a purified toxin. Molec. Microbiol. 3:1533-1543.

Ausubel et al., eds. (1995) *Current Protocols in Molecular Biology*, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Bown, D. P., Wilkinson, H. S., Jongsma, M. A., Gatehouse, J. A. (2004) Characterization of cysteine proteinases responsible for digestive proteolysis in guts of larval western corn rootworm (*Diabrotica virgifera*) by expression in the yeast *Pichia pastoris*. Insect Biochem. Molec. Biol. 34:305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia Sinica 18:659-668.

Crameri, A., Cwirla, S., Stemmer, W. P. C. (1996a) Construction and evolution of antibody-phage libraries by DNA shuffling. Nat. Med. 2:100-103.

Crameri, A., Whitehom, E. A., Tate, E., Stemmer, W. P. C. (1996b) Improved green fluorescent protein by molecular evolution using DNA shuffling. Nat. Biotech. 14:315-319.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crickmore N., Zeigler, D. R., Feitelson J., Schnepf, E., Van Rie J., Lereclus D., Baum J., and Dean D. H. (1998) Revision of the Nomenclature for the *Bacillus thuringiensis* Pesticidal Crystal Proteins Microbiol. Mol. Biol. Reviews 62:807-813.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Ellis, R. T., Stockhoff, B. A., Stamp, L., Schnepf, H. E., Schwab, G. E., Knuth, M., Russell, J., Cardineau, G. A., Narva, K. E. (2002) Novel *Bacillus thuringiensis* binary insecticidal crystal proteins active on western corn rootworm, *Diabrotica virgifera virgifera* LeConte. Appl. Environ. Microbiol. 68:1137-1145.

Englemann, F., Geraerts, W. P. M., (1980) The proteases and the protease inhibitor in the midgut of *Leucophaea maderae*. J. Insect Physiol. 261:703-710.

Fraley, R. T., Rogers, S. G., Horsch, R. B. (1986) Genetic transformation in higher plants. Crit. Rev. Plant Sci. 4:1-46.

Gaertner, F. H., Quick, T. C. & Thompson, M. A. 1993. CellCap: An encapsulation system for Insecticidal Biotoxin Proteins. In: KIM, L. (ed.) *Advanced Engineered Biopesticides*. New York: Marcel Dekker Inc.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on CryIA(c). J. Biol. Chem. 266:17954-17958.

Gillikin, J. W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Haider, M. Z., Knowles, B. H., Ellar, D. J. (1986) Specificity of *Bacillus thuringiensis* var. *colmeri* insecticidal δ-endotoxin is determined by differential proteolytic processing of the protoxin by larval gut proteases. Eur. J. Biochem. 156:531-540.

Heckel, D. G., Gahan, L. J., Baxter, S. W., Zhao, J-Z., Shelton, A. M., Gould, F., Tabashnik, B. E. (2007) The diversity of Bt resistance genes in species of *Lepidoptera*. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131:2961-2969.

Hoagland, D. R., Arnon, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) Structural and functional analysis of a cloned delta endotoxin of *Bacillus thuringiensis* berliner 1715. Eur. J. Biochem. 161:273-280.

Honée, G., Convents, D., Van Rie, J., Jansens, S., Peferoen, M., Visser, B. (1991) The C-terminal domain of the toxic fragment of a *Bacillus thuringiensis* crystal protein determines receptor binding. Mol. Microbiol. 5:2799-2806

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (*Lepidoptera*: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272:1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Linsmaier, E. M., Skoog, F. (1965) Organic growth factor requirements of tobacco tissue. Physiologia Plantarum 18:100-127.

Littlefield, J. W. (1964) Selection of hybrids from matings of fibroblasts in vitro and their presumed recombinants. Science 145:709-710.

Meinkoth, J., Wahl, G. (1984) Hybridization of nucleic acids immobilized on solid supports. Anal. Biochem. 138:267-284.

Metcalf, R. L. (1986) The ecology of insecticides and the chemical control of insects. pp. 251-297. In (Marcos Kogan (ed.)) Ecological theory and integrated pest management practice. John Wiley & Sons, N.Y. 362 pp.

Moellenbeck, D. J., Peters, M. L., Bing, J. W., Rouse, J. R., Higgins, L. S., Sims, L., Nevshemal, T., Marshall, L., Ellis, R. T., Bystrak, P. G., Lang, B. A., Stewart, J. L., Kouba, K., Sondag, V., Gustafson, V., Nour, K., Xu, D., Swenson, J., Zhang, J., Czapla, T., Schwab, G., Jayne, S., Stockhoff, B. A., Narva, K., Schnepf, H. E., Stelman, S. J., Poutre, C., Koziel, M., Duck, N. (2001) Insecticidal proteins from *Bacillus thuringiensis* protect corn from corn rootworms. Nat. Biotech. 19:668-672.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado Potato Beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun 362:437-442.

Pigott, C. R., Ellar, D. J. (2007) Role of receptors in *Bacillus thuringiensis* crystal toxin activity. Microbiol. Molec. Biol. Rev. 71:255-281.

Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified Bt toxins to counter insect resistance. Science 318:1640-1642.

Squires, C. H., Retallack, D. M., Chew, L. C., Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encyclopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown (ed.), Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to Bt crops: evidence versus theory. Nat. Biotech. 26:199-202.

Taggart, R. T., Samloff, I. M. (1983) Stable antibody-producing murine hybridomas. Science 219:1228-1230.

Thie, N. M. R., Houseman J. G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Varshaysky, A. (1997) The N-end rule pathway of protein degradation. Genes to Cells 2:13-28.

Vaughn, T., Cavato, T., Brar, G., Coombe, T., DeGooyer, T., Ford, S., Groth, M., Howe, A., Johnson, S., Kolacz, K., Pilcher, C., Prucell, J., Romano, C., English, L., Pershing, J. (2005) A method of controlling corn rootworm feeding using a *Bacillus thuringiensis* protein expressed in transgenic maize. Crop. Sci. 45:931-938.

Walters, F. S., Slatin, S. L., Kulesza, C. A., English, L. H. (1993) Ion channel activity of N-terminal fragments from CryIA(c) delta-endotoxin. Biochem. Biophys. Res. Commun 196:921-926.

Walters, F. S., Stacy, C. M., Lee, M. K., Palekar, N., Chen, J. S. (2008) An engineered chymotrypsin/cathepsin G site in domain I renders *Bacillus thuringiensis* Cry3A active against western corn rootworm larvae. Appl. Environ. Microbiol. 74:367-374.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. (eds.) (2002) *Arabidopsis*: A Laboratory Manual. Cold Spring Harbor Press, Cold Spring Harbor, N.Y., 354 pages.

Witkowski, J. F., Wedberg, J. L., Steffey, K. L., Sloderbeck, P. E., Siegfried, B. D., Rice, M. E., Pilcher, C. D., Onstad, D. W., Mason, C. E., Lewis, L. C., Landis, D. A., Keaster, A. J., Huang, F., Higgins, R. A., Haas, M. J., Gray, M. E., Giles, K. L., Foster, J. E., Davis, P. M., Calvin, D. D., Buschman, L. L., Bolin, P. C., Barry, B. D., Andow, D. A., Alstad, D. N. (2002) Bt corn and European Corn Borer (Ostlie, K. R., Hutchison, W. D., Hellmich, R. L. (eds)). University of Minnesota Extension Service. Publ. WW-07055.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

We claim:

1. A pesticide formulation comprising a pesticidal effective amount of DIG-17 insecticidal toxin polypeptide having growth inhibitory activity against Coleopteran insects, wherein the polypeptide comprises a core toxin segment that includes residues 2 to 666 of SEQ ID NO:5 linked to a C-terminal protoxin portion of a Cry toxin other than DIG-17.

2. The pesticide formulation of claim 1, wherein the polypeptide is a chimeric protein and the C-terminal protoxin portion of cry1Ab or a cry1Ac/cry1Ab chimeric toxin.

3. The pesticide formulation of claim 2, wherein the C-terminal protoxin portion comprises the C-terminal protoxin portion of Cry1Ab.

4. The pesticide formulation of claim 3, wherein the C-terminal protoxin portion comprises the C-terminal protoxin portion of cry1Ac/cry1Ab chimeric toxin.

5. A method for controlling a Coleopteran pest population comprising contacting said population with a pesticidally effective amount of a DIG-17 insecticidal toxin polypeptide having growth inhibitory activity against Coleopteran insects, wherein the polypeptide comprises a core toxin segment that includes residues 2 to 666 of SEQ ID NO:5.

6. The method of claim 5, wherein the pest population is a Colorado potato beetle population.

7. A nucleic acid construct, wherein the construct comprises a heterologous nucleic acid sequence that is recombinantly linked to a sequence encoding a DIG-17 insecticidal toxin polypeptide having growth inhibitory activity against Coleopteran insects, wherein the polypeptide comprises a core toxin segment that includes residues 2 to 666 of SEQ ID NO:5, and wherein the heterologous nucleic acid sequence is a promoter, enhancer, multiple cloning site, or vector sequence, or protoxin portion of a Cry toxin other than DIG-17.

8. The nucleic acid construct of claim 7, wherein the heterologous nucleic acid sequence is a promoter sequence capable of driving expression in a plant and the promoter is operably linked to the sequence encoding the DIG17 insecticidal toxin polypeptide.

9. The nucleic acid construct of claim 8, wherein the sequence encoding the core toxin segment is codon-optimized for expression in a plant.

10. The nucleic acid construct of claim 9, wherein the promoter is capable of driving expression in corn and the sequence encoding the DIG-17 core toxin segment is codon optimized for expression in corn.

11. The nucleic acid construct of claim 7, wherein the sequence encoding the polypeptide comprises SEQ ID NO:1, SEQ ID NO:3, SEQ ID NO:4, or SEQ ID NO:6.

12. The nucleic acid construct of claim 11, wherein the construct is a vector.

13. The nucleic acid construct of claim 11, wherein the construct is a vector and the nucleic acid sequence encoding the core toxin segment is linked to a sequence encoding C-terminal protoxin portion of a Cry toxin other than DIG-17.

14. The nucleic acid construct of claim 13, wherein the nucleic acid sequence encoding the core toxin segment is linked to a sequence encoding a C-terminal protoxin portion of Cry1Ab or a C-terminal protoxin portion of cry1Ac/cry1Ab chimeric toxin.

15. The nucleic acid construct of claim 9, wherein the construct comprises a promoter and the promoter is capable of driving expression in potato and the sequence encoding the polypeptide is codon optimized for expression in potato.

16. A transgenic plant comprising the nucleic acid construct of claim 7.

17. A transgenic plant comprising the nucleic acid construct of claim 11.

* * * * *